United States Patent

Nakano et al.

[11] Patent Number: 5,355,398
[45] Date of Patent: Oct. 11, 1994

[54] ROTATIONAL TOMOGRAPHIC X-RAY APPARATUS WITH PLANIGRAPH FUNCTION

[75] Inventors: Kohzo Nakano; Keisuke Mori; Eiichi Arai; Takeshi Kusunoki; Takahiro Yoshimura; Masanori Otsuka, all of Kyoto, Japan

[73] Assignee: Kabushiki Kaisha Morita Seisakusho, Kyoto, Japan

[21] Appl. No.: 54,399

[22] Filed: Apr. 27, 1993

[30] Foreign Application Priority Data

Apr. 30, 1992 [JP] Japan .................. 4-139888

[51] Int. Cl.⁵ .............................. A61B 6/14
[52] U.S. Cl. ......................... 378/39; 378/38; 378/40
[58] Field of Search .............. 378/38, 39, 40, 25, 378/21, 27, 115, 193, 195, 196, 197

[56] References Cited

U.S. PATENT DOCUMENTS

| | | | |
|---|---|---|---|
| 3,673,408 | 6/1972 | Moss | 378/39 |
| 4,242,585 | 12/1980 | Yamano | 378/39 |
| 4,365,340 | 12/1982 | Nishikawa et al. | 378/39 |
| 4,847,881 | 7/1989 | Heubeck | 378/40 X |
| 4,920,573 | 4/1990 | Rhodes et al. | 378/40 X |
| 5,093,852 | 3/1992 | Nishikawa et al. | 378/39 |

Primary Examiner—David P. Porta
Attorney, Agent, or Firm—Koda and Androlia

[57] ABSTRACT

A rotational tomographic X-ray apparatus is disclosed as having an X-ray detection surface disposed parallel to a planigraphic plane selected as a subject to be photographed, and comprising a mechanism for linearly moving the X-ray generator and the X-ray detection surface of the apparatus in relatively opposite directions parallel to the planigraphic plane with the head of a patient positioned therebetween, and for controlling the irradiation direction of X-rays so that the irradiated X-rays always pass the same specific region in the planigraphic plane and are incident on the X-ray detection surface in synchronization with the linear movement. With this apparatus, clear planigraphic photographing with no distortion is possible and the magnifying ratios of X-ray images can be changed easily.

18 Claims, 18 Drawing Sheets

ROTATIONAL TOMOGRAPHIC X-RAY APPARATUS WITH PLANIGRAPH FUNCTION

BACKGROUND OF THE INVENTION

1. Field of the Invention

The present invention relates to a tomographic X-ray apparatus for dental and otolaryngological diagnosis for photographing the head or maxillofacial region of a patient.

2. Description of the Prior Art

Dental rotational tomographic X-ray apparatuses, generally referred to as dental panoramic X-ray apparatuses in the field of dental diagnosis, are known and used widely even at small dental clinics. The general types of these apparatuses comprise an X-ray source and an X-ray film disposed at opposite ends of a rotary arm, with the head of a patient positioned therebetween. The rotary arm is not necessarily to be formed in the shape of a slender rod. A ring-shaped rotary arm is also known as described in U.S. Pat. No. 4,847,881 for example.

These days, in addition to the above-mentioned rotational tomographic X-ray apparatuses, there have been demands for planigraphic X-ray apparatuses for selectively photographing specific regions in narrow tomographic widths. Such planigraphic X-ray apparatuses conventionally used for general medical diagnosis are large in size and thus require a wide installation space. In addition, they are expensive despite of having a single-purpose function only. Accordingly, the conventional apparatuses have not been used widely at general dental clinics other than relatively large-sized hospitals.

As the above-mentioned conventional planigraphic X-ray apparatuses, various types are known, such as a tomography type wherein the X-ray source and the film supported by a rotary arm perform symmetric rotational motions around the rotation center of the rotary arm, a planigraphy type wherein the X-ray source and the film perform linear motions in parallel and a multiple track type wherein the X-ray source and the film perform motions along curved tracks. These types, however, have relatively wide photographing areas so that they can be used to mainly photograph abdominal regions. In addition, the rotary arm of each of these types is rotated around a fixed point. For these reasons, it is difficult to change the magnifying ratio of the X-ray image to be obtained. Furthermore, it is necessary to preserve a rotation range for the rotary arm, causing the problem of requiring a wide installation space.

Accordingly, these days, X-ray apparatuses having various photographing functions have been proposed for the purpose of diagnosis in dental, otolaryngological and oral surgery fields.

Japanese Laid-open Patent Application No. 58-165825, for example, discloses an apparatus which is capable of performing both planigraphic photographing and rotational tomographic photographing. This apparatus, however, has no means for controlling the rotation angle of the X-ray generator thereof. In addition, when the apparatus performs planiographic photographing, the film transfer mechanism thereof is stopped and the rotary arm is rotated, and then the entire region of an X-ray image is exposed once while the film is held stationary. With this method, distortion is apt to be caused in photographed X-ray images, and the magnifying ratio of the X-ray image to be obtained in the case of planigraphic photographing cannot be changed.

The apparatus disclosed by the above-mentioned U.S. Pat. No. 4,847,881 can perform rotational tomographic photographing of dental arches and obtain slice tomogram images of temporomandibular joints. The slice tomogram method used for this apparatus, however, is not classified as planigraphic photographing but classified as rotational tomographic photographing having a narrow tomographic width. Besides, since the apparatus has no mechanism for planigraphic photographing, it cannot perform planigraphic photographing.

SUMMARY OF THE INVENTION

In view of the foregoing problems, it is an object of the present invention to provide an apparatus capable of performing clear planigraphic photographing without causing any distortion, equipped with a function for changing the magnifying ratios of X-ray images, and yet being inexpensive enough to allow easy introduction to small clinics. The apparatus of the present invention is also intended to be capable of simply performing planigraphic photographing for tomographic planes in any direction.

In the basic structure of the conventional rotational tomographic X-ray apparatus, the X-ray generator and the X-ray detection surface such as an X-ray film cassette are disposed opposite to each other with the head of a patient positioned therebetween, and they are rotated around the patient while a constant relationship is maintained therebetween. The X-ray detection surface is moved perpendicular to the irradiation direction of the X-rays from the X-ray generator in synchronization with the rotation so that panoramic X-ray images of curved tomographic planes, such as a dental arch for example, can be obtained. The apparatus of the present invention has functions and means added to the above-mentioned structure of the conventional type. More particularly, the apparatus of the present invention has an X-ray detection surface disposed parallel to a planigraphic plane selected as a subject to be photographed, and equipped with a linear movement means for synchronously moving the X-ray generator and the X-ray detection surface in the directions relatively opposite to each other and parallel to the above-mentioned planigraphic plane, and an X-ray irradiation direction control means for controlling the irradiation direction of X-rays so that the X-rays always pass the same specific region in the above-mentioned planigraphic plane and are incident on the X-ray detection surface in synchronization with the parallel movement.

In addition, the apparatus of the present invention is equipped with a support member for supporting the X-ray generator and the X-ray detection surface disposed opposite to each other with the planigraphic plane positioned therebetween. In this structure of the apparatus of the present invention, the linear movement means moves both the X-ray generator and the X-ray detection surface linearly relative to the support member, and the X-ray irradiation direction control means rotates the X-ray generator toward the X-ray detection surface.

Furthermore, the above-mentioned structure can be modified so that the support member can be moved linearly parallel to the planigraphic plane by using the linear movement means. In this case, the apparatus of the present invention can have various structures: a first structure wherein both or one of the X-ray generator and the X-ray detection surface is moved linearly relative to the support member, a second structure wherein the X-ray generator is moved together with the support member and only the X-ray detection surface is moved linearly relative to the support member, and a third structure wherein the X-ray detection surface is moved together with the support member and only the X-ray generator is moved linearly relative to the support member.

The general type of the conventional rotational tomographic X-ray apparatus is equipped with the rotary arm, and the X-ray generator is held at one end of the rotary arm and the X-ray detection surface is held at the other end thereof. It is, therefore, possible to use the rotary arm as the above-mentioned support member. In this case, since the conventional type is generally equipped with a mechanism for positioning control of rotation center which is used to control the rotation center of the rotary arm, this mechanism can be used as the linear movement means for moving the rotary arm without making any modification. It is desired to provide a rotation means for rotating the mechanism for positioning control of potation center. If the mechanism for positioning control of rotation center cannot be used to linearly move the rotary arm, it is desired to provide a means for linearly moving the mechanism for positioning control of rotation center.

Moreover, it is desired to provide an irradiation field shape changeover means, which is used to change the irradiation shape of the X-ray beam to be irradiated from the X-ray generator depending on the mode of photographing, on the side of the X-ray generator. It is also desired to provide a beam-receiving shape changeover means, which is used to change the receiving shape of the X-ray beam to be incident on the X-ray detection surface depending on the mode of photographing, on the side of the X-ray detection surface. In this case, it is possible to provide a movement means which automatically moves the beam-receiving shape changeover means in synchronization with the movement of the X-ray detection surface.

An X-ray film cassette or an X-ray radiographic photosensitive element can be used as the X-ray detection surface. An X-ray CCD, an X-ray photoelectric conversion device or an X-ray fluorescent image intensifier can also be used as the X-ray detection surface. In the latter case, it is possible to move the detection region of such a device by electrically processing X-ray images, instead of moving the device mechanically.

As described above, the apparatus of the present invention can be provided by adding a movement means for synchronously moving the X-ray generator and the X-ray detection surface parallel to a planigraphic plane with the planigraphic plane positioned therebetween, and also by adding an X-ray irradiation direction control means for controlling irradiated X-rays so that they always pass the same specific region in the planigraphic plane and ape incident on the X-ray detection surface in synchronization with the above-mentioned movement, to the conventional, generally used rotational tomographic X-ray apparatus (so-called dental panoramic X-ray apparatus). Consequently, by the addition, a relatively small and inexpensive rotational tomographic X-ray apparatus with planigraph function can be realized, which can generate X-ray images with less distortion and can change the magnifying ratios of X-ray images as necessary.

In particular, in the case of the apparatus wherein the X-ray generator and the X-ray detection surface are disposed at opposite ends of the rotary arm, the desired object of the present invention can be accomplished by moving the rotary arm parallel to the planigraphic plane. Furthermore, the structure for planigraphic photographing can be simplified by utilizing the mechanism for positioning control of rotation center for moving the rotary arm of a known dental panoramic X-ray apparatus to move the rotary arm parallel to the planigraphic plane. Moreover, by providing a rotation means for rotating the mechanism for positioning control of rotation center, photographing is easily possible in any direction of the planigraphic plane, thereby also making the setting of the patient's head easy.

Additionally, by providing the irradiation field shape changeover means and the beam-receiving shape changeover means, the cross-sectional shape of the X-ray beam suited for a desired photographing mode can be obtained.

BRIEF DESCRIPTION Of THE DRAWINGS

FIGS. 13 to 16 are schematic views illustrating the structures of the mechanisms for positioning control of rotation center for still other embodiments; FIGS. 13(a) to 16(a) are plan views illustrating the mechanisms and FIGS. 13(b) to 16(b) are cross-sectional views taken on line A—A of FIGS. 13(a) to 16(a) respectively.

FIG. 17 is a schematic view illustrating the structure of the mechanism for positioning control of rotation center of another embodiment.

FIG. 18 is a schematic view illustrating the structure of the mechanism for positioning control of rotation center of still another embodiment.

DETAILED DESCRIPTION OF THE PREFERRED EMBODIMENTS

An embodiment of the present invention will be explained below referring to the accompanying drawings.

Figure 1:
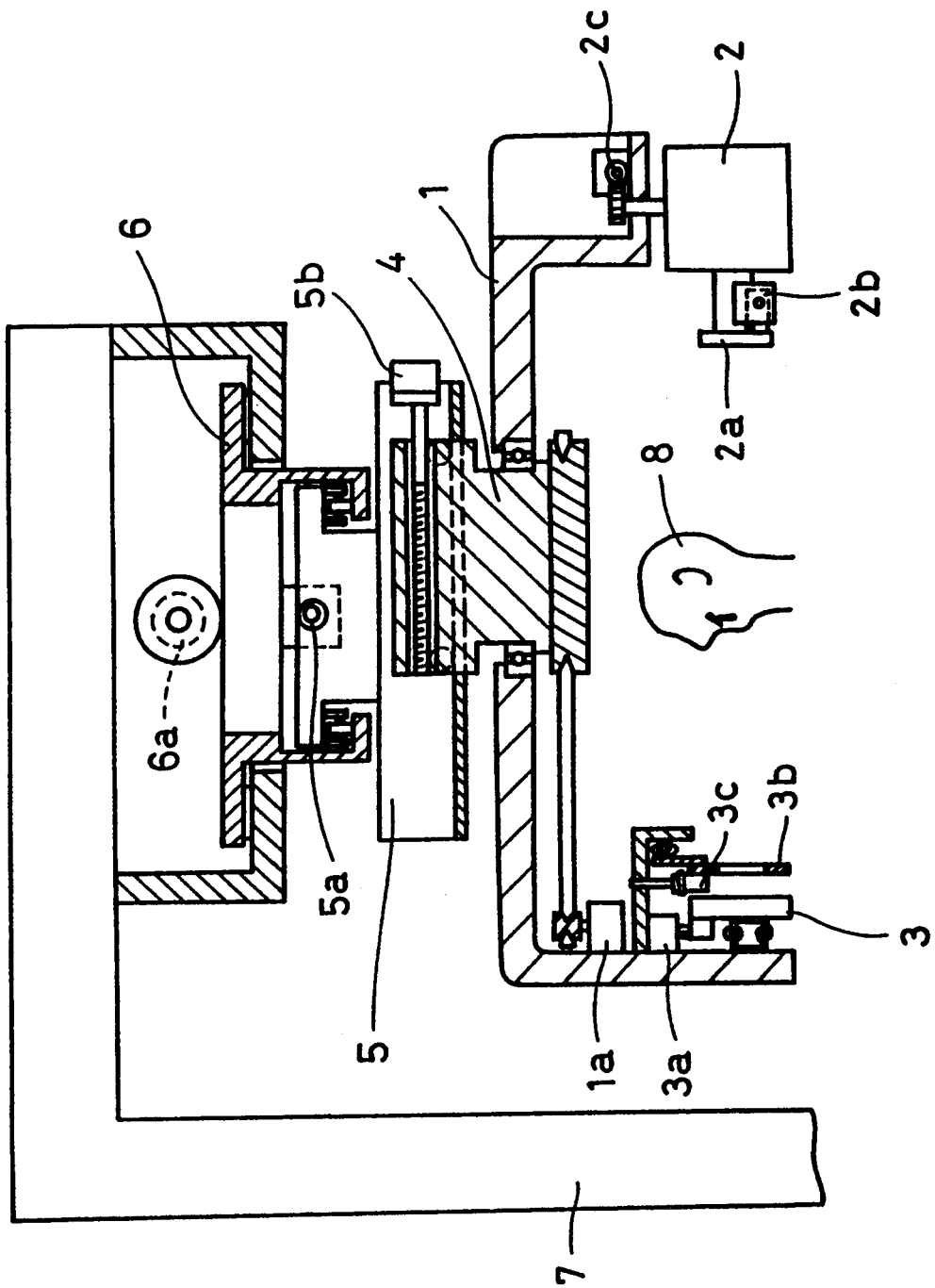
FIG. 1 is a fragmentary schematic side view illustrating an embodiment of an apparatus in accordance with the present invention, taken on line A—A of FIG. 2.
Figure 2:
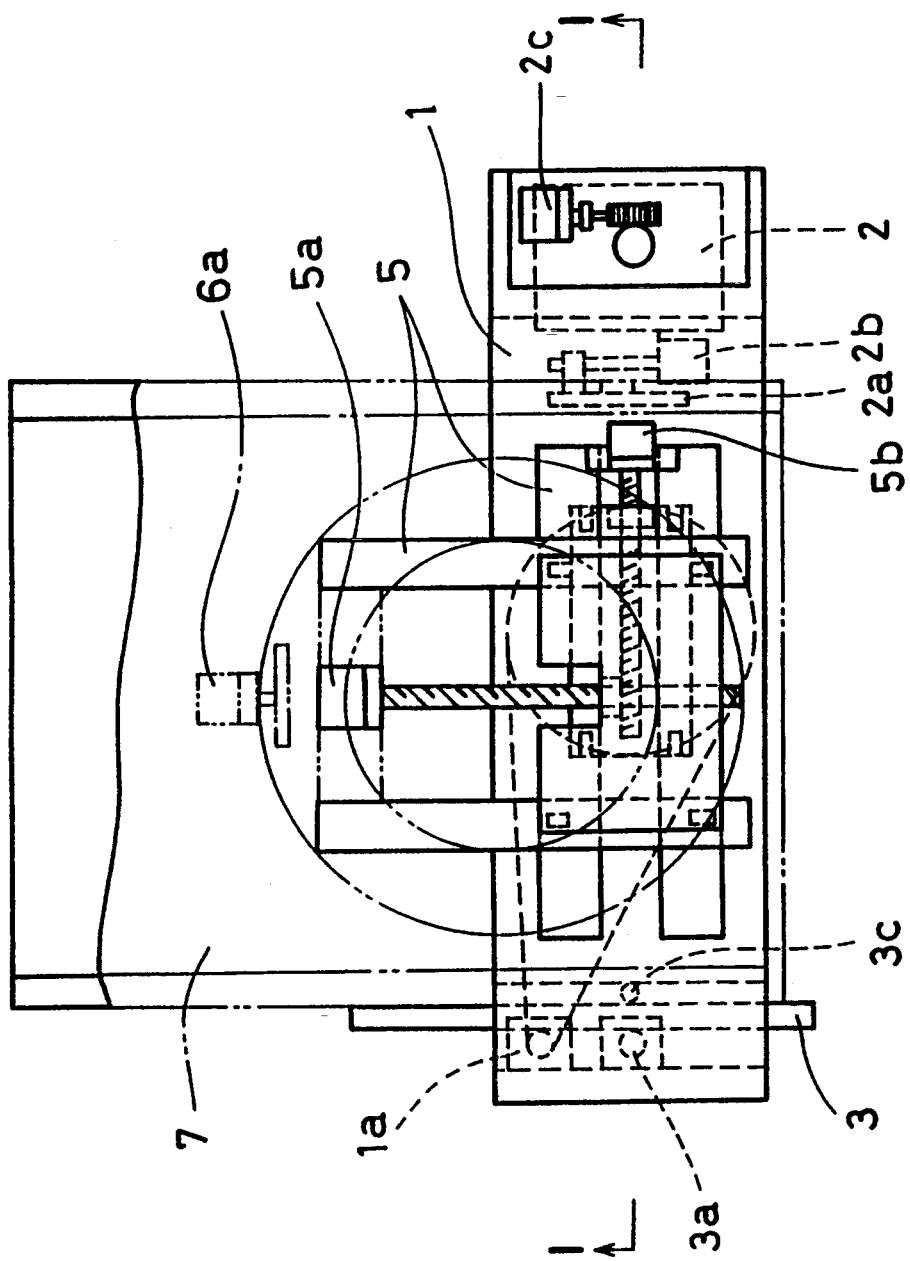
FIG. 2 is a schematic plan view illustrating the embodiment shown in FIG. 1.

Referring to FIGS. 1 and 2 which are schematic views of the embodiment of the present invention, numeral 1 represents a rotary arm, numeral 2 represents an X-ray source supported at one end of the rotary arm 1, numeral 3 represents an X-ray film cassette supported at the other end of the rotary arm 1, numeral 4 represents a rotation shaft of the rotary arm 1, numeral 5 represents an X-Y table for supporting the rotation shaft 4, numeral 6 is a rotation base for supporting the X-Y table 5, numeral 7 represents a pedestal base for supporting the rotation base 6, and numeral 8 represents the head of a patient (the subject to be photographed).

The rotary arm 1 is rotated in a horizontal plane by a rotation drive motor 1a. The position of the rotation shaft 4 is controlled by the operation of the X-axis movement drive motor 5a and the Y-axis movement drive motor 5b of the X-Y table 5. The rotation base 6 rotates relative to the pedestal base 7 when the rotation drive motor 6a is activated, thereby rotating the X-Y table 5.

The X-ray source 2 comprises an irradiation field shape changeover plate 2a for changing the irradiation field shape of X-rays, an irradiation field shape changeover motor 2b for operating the changeover plate 2a and a direction control motor 2c for rotating the X-ray source 2 in a horizontal plane via a worm gear unit. The X-ray film cassette 3 comprises a cassette movement drive motor 3a, a beam-receiving shape changeover plate 3b for changing the beam-receiving shape of X-rays and a beam-receiving changeover plate drive motor 3c for driving the changeover plate 3b. The irradiation field shape changeover plate 2a is structured to change the shape of the opening thereof by moving such a slit plate as that disclosed by Japanese Patent Publication No. 3-73306 for example, or by moving and combining such two slit plates as those disclosed by Japanese Laid-open Utility Model Application No. 2-39705 for example. The beam-receiving shape changeover plate 3b can also be structured in a manner similar to that for the irradiation field shape changeover plate 2a.

The entire basic structure of the embodiment of the present invention is described above. To make planigraphic photographing possible, the embodiment is equipped with the rotation base 6, the structure for rotating the X-ray source 2 in a horizontal plane by using the direction control motor 2c, the beam-receiving shape changeover plate 3b for changing the beam-receiving shape of X-rays at the film cassette 3 and the beam-receiving shape changeover plate drive motor 3c, all of which are not provided for the conventional panoramic X-ray apparatus. Aside from these additional devices, the structure of the embodiment is basically the same as the known structure of the conventional panoramic X-ray apparatus.

Figure 3:
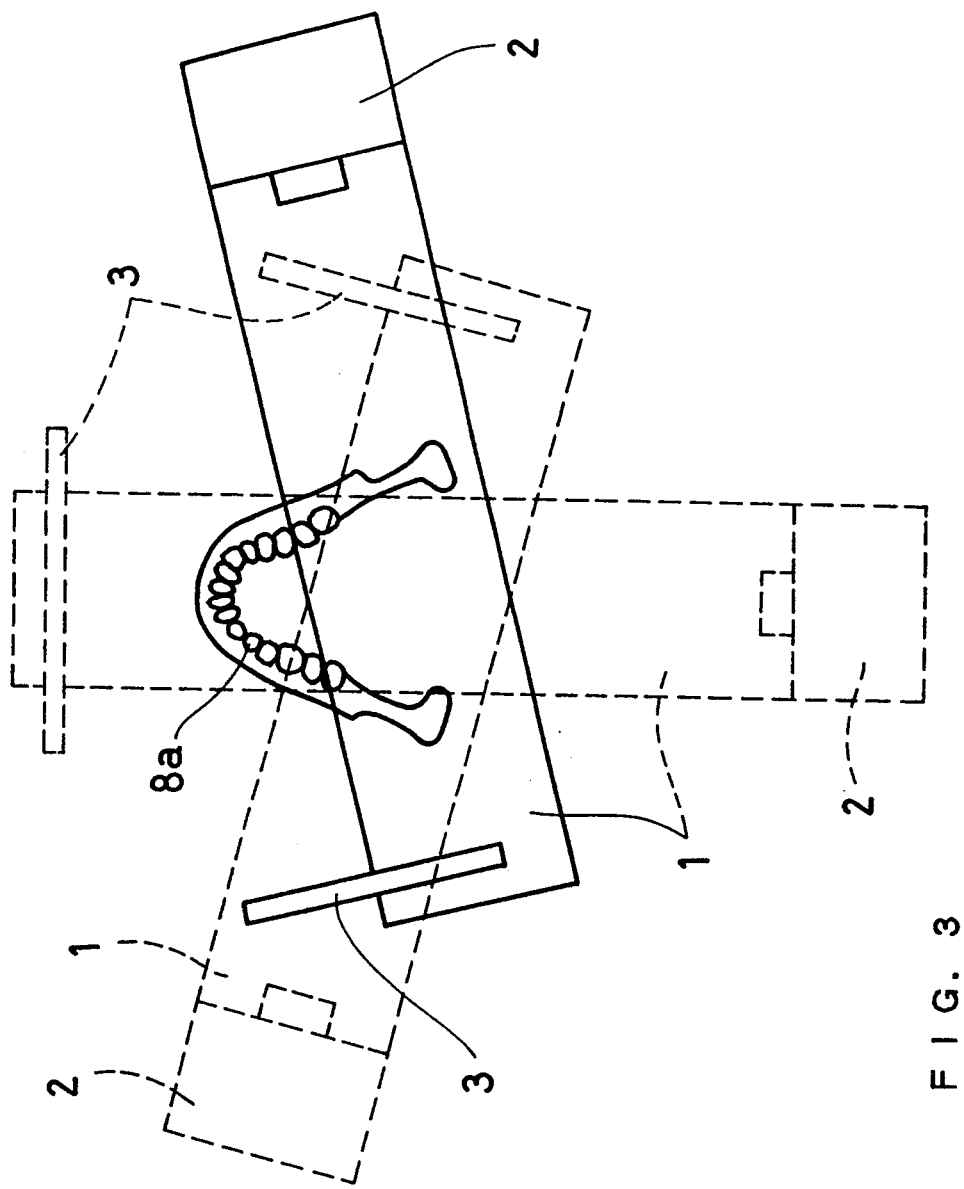
FIG. 3 is a view illustrating rotational tomographic photographing by using the embodiment.

When performing rotational tomographic photographing of all entire jaw by using this apparatus, the X-ray beam to be irradiated from the X-ray source 2 is set to a vertically narrow beam by the irradiation field shape changeover plate 2a driven by the motor 2b, and the rotary arm 1 is rotated around the dental arch 8a of the patient as shown in FIG. 3. In synchronization with this rotation, the rotation shaft 4 is moved in response to the progress of rotational tomographic photographing of the entire jaw. The film cassette 3 is also moved perpendicular to the longitudinal axis of the rotary arm 1 in synchronization with the rotation velocity of the rotary arm 1 to obtain an X-ray image which is generally known as a panoramic X-ray image of the entire jaw including the dental arch 8a.

Figure 4:
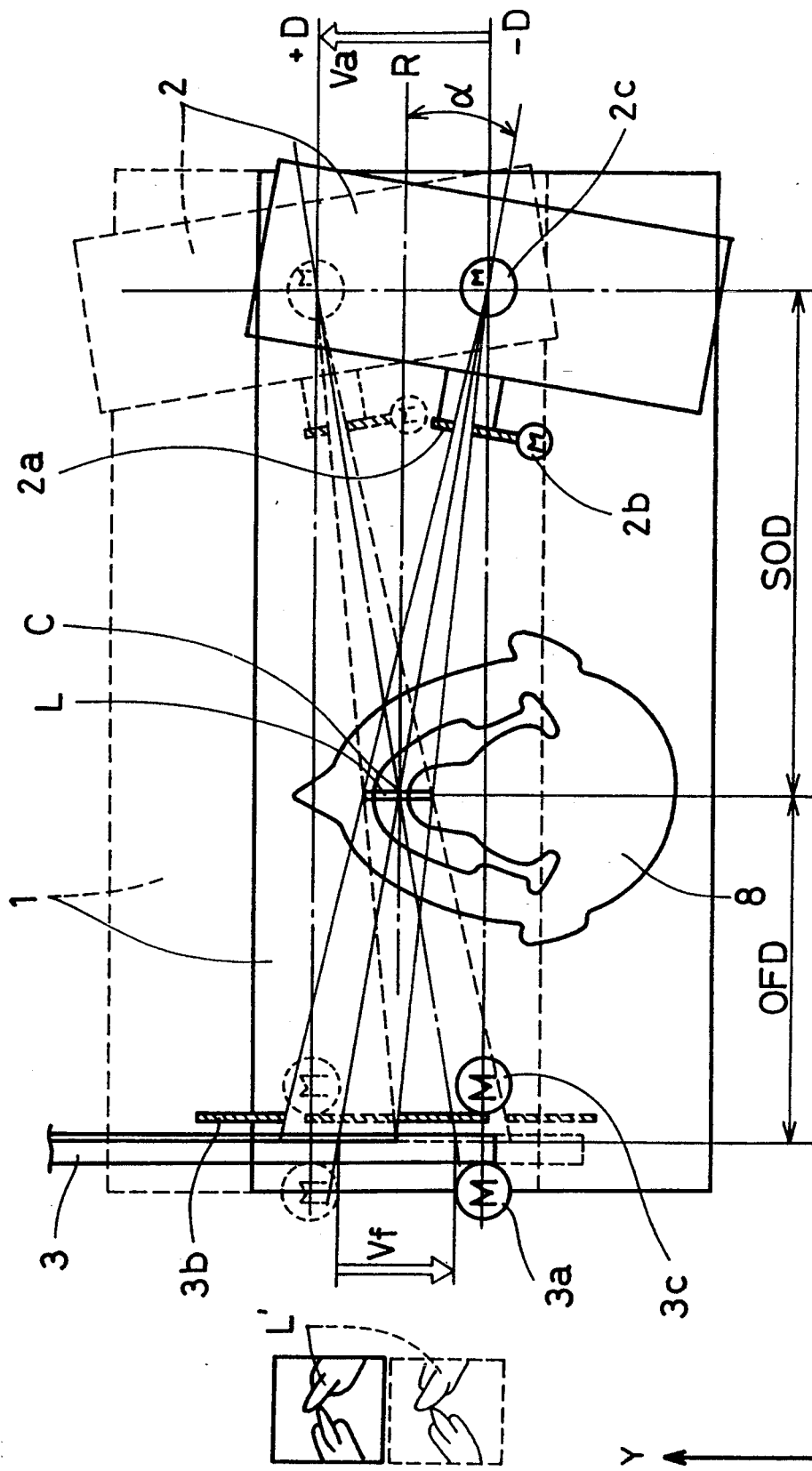
FIG. 4 is a view illustrating planigraphic photographing of a plane by using the embodiment.

FIG. 4 illustrates planigraphic photographing performed by using this apparatus. The left-and-right direction of the patient is called "X axis" and the back-and-forth direction thereof is called "Y axis" for reasons of convenience, and the apparatus is assumed to be operated as described below to make the explanation of operation simple. Letter L represents a planigraphic plane selected as a subject to be photographed, and this plane is parallel to the Y axis in this example.

First, the rotary arm 1 is set so that the longitudinal axis thereof is parallel to the X axis and the central line thereof is displaced by a distance of $-D$ from the reference line R. The irradiation field shape changeover plate 2a is changed so that the irradiation field of X-rays has a rectangular shape wider than that used at the time of rotational tomographic photographing of the dental arch, and the direction of the X-ray source 2 is set by the direction control motor 2c so that the central axis of the X-ray beam passes the center C of the planigraphic plane L. The film cassette 3 is set at the position indicated by the solid lines in the figure by the movement drive motor 3a so that the film cassette 3 can always receive the X-ray beam at the same film position in synchronization with the movement of the above-mentioned X-ray beam. The shape of the beam-receiving shape changeover plate 3b is automatically changed by the motor 3c so that the X-ray incident portion thereof is opened depending on the shape and size of the planigraphic plane L.

After these conditions, planigraphic photographing is performed by moving the rotary arm 1, wherein the X-ray source 2 and the film cassette 3 are supported at the opposite ends thereof, in the Y-axis direction, that is, in the direction parallel to the planigraphic plane L at a constant velocity by using the X-Y table shown in FIG. 1, by rotating the X-ray source 2 relative to the rotary arm 1 in synchronization with the movement of the rotary arm 1 in the Y-axis direction, and by moving the film cassette 3 at a constant velocity in synchronization with the movement of the rotary arm 1. During this photographing operation, the film cassette 3 is controlled to move so that the central axis of the X-ray beam irradiated from the X-ray source 2 always passes the center C of the planigraphic plane L, and the opening of the beam-receiving shape changeover plate 3b is moved unitedly with the film cassette 3 relative to the rotary arm 1 by the motor 3c.

Assuming that the Y-axis direction movement velocity of the X-ray source 2 supported by the rotary arm 1 is Va, the distance in the X-axis direction from the planigraphic plane L to the X-ray generator section of the X-ray source 2 is SOD, the distance in the X-axis direction from the planigraphic plane L to the film surface of the film cassette 3 is OFD, the movement velocity of the film cassette 3 is Vf, the rotation angle of the central axis of the X-ray beam irradiated from the X-ray source 2 relative to the X-axis is $\alpha$, and the time elapsed is t:

$$\tan \alpha = (-D + Va \times t)/SOD$$

$$Vf = -Va \times OFD/SOD$$

The following control is performed so that the above equations can be established; the rotary arm 1, wherein the X-ray source 2 and the film cassette 3 are supported at the opposite ends thereof, is moved in the Y-axis direction, that is, parallel to the planigraphic plane L by the X-Y table 5 shown in FIG. 1, the X-ray source 2 is rotated relative to the rotary arm 1 in synchronization with the movement of the rotary arm 1 and the film cassette 3 is moved relative to the rotary arm 1.

By this control, the X-ray image L' of the planigraphic plane L is obtained always at the same film position of the film cassette 3 as shown at the left end of FIG. 4. On the other hand, the X-ray images existing in the middle of the route of the X-ray beam, other than the X-ray image of the planigraphic plane L, move on the film surface, resulting in bluffed images. Consequently, the X-ray image L' of the planigraphic plane L can be photographed. The negative sign of the movement velocity of the film cassette 3 indicates that the film cassette 3 moves in the direction opposite to the movement direction of the rotary arm 1.

The above-mentioned photographing method greatly differs from the conventional planigraphic photographing method in that the rotary arm 1 is not rotated. Since the magnifying ratio of the X-ray image to be obtained is determined by the ratio of distance SOD to distance OFD, the rotation center of the rotary arm must be moved to change the magnifying ratio in the case of the conventional apparatus. This makes the control method troublesome and also makes the structure of the apparatus complicated. For this reason, the magnifying ratio cannot be changed easily in the case of the conventional apparatus. In the case of the embodiment of the present invention, however, since the rotary arm 1 is not rotated, the magnifying patio can be changed easily and continuously by performing control so that the rotation velocity of the X-ray source 2 and the movement velocity of the film cassette 3 can be changed in a constant relationship with the movement velocity of the rotary arm 1 depending on the ratio of the distances.

Furthermore, since the rotary arm 1 is not rotated, the space required for this embodiment during operation can be ,lade smaller than that of the conventional apparatus, and the rotation angle of the X-ray source 2 relative to the rotary arm 1 can be controlled easily. Moreover, the film cassette 3 can be disposed perpendicular to the longitudinal axis of the rotary arm 1, and a linear constant-velocity motion can be used for the movement of the film cassette 3. These make the setting of the positional relationship to the planigraphic plane L easy. As a result, highly accurate control is achieved easily by using relatively simple mechanisms.

Figure 5:
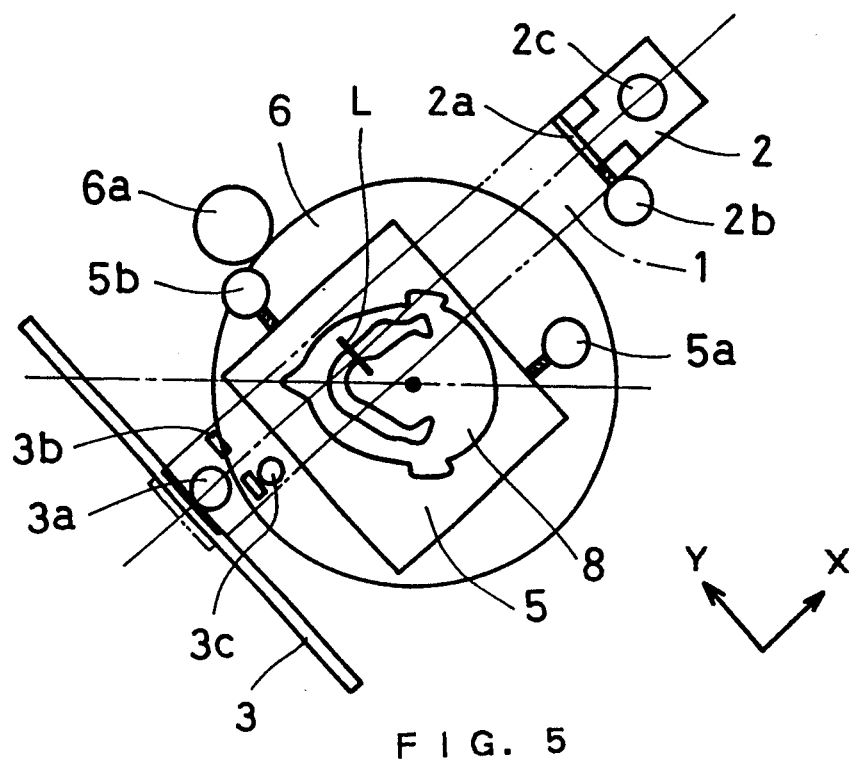
FIG. 5 is a view illustrating planigraphic photographing of another plane by using the embodiment.

FIG. 4 shows an example wherein the transverse plane of the patient's front tooth region is used as the planigraphic plane L. In this case, it is easy to position the planigraphic plane L parallel to the Y-axis, and the rotary arm 1 can be moved in the Y-axis axis direction by using only the Y-axis movement drive motor 5b of the X-Y table 5. On the other hand, when the planigraphic plane L is inclined relative to the direction of the head 8 of the patient, that is, when the molar region is photographed for example, the rotation base 6 is rotated by activating the motor 6a, instead of changing the direction of the patient or repositioning the patient, and the Y axis of the X-Y table 5 is set parallel to the planigraphic plane L as shown in FIG. 5. After this setting, photographing is performed in the same way as described above. In this way, such an inclined planigraphic plane L can also be photographed easily by rotating the X-Y table itself via the rotation base 6 provided additionally. This method also makes the setting of the apparatus easier than the method wherein the patient is moved.

Figure 6:
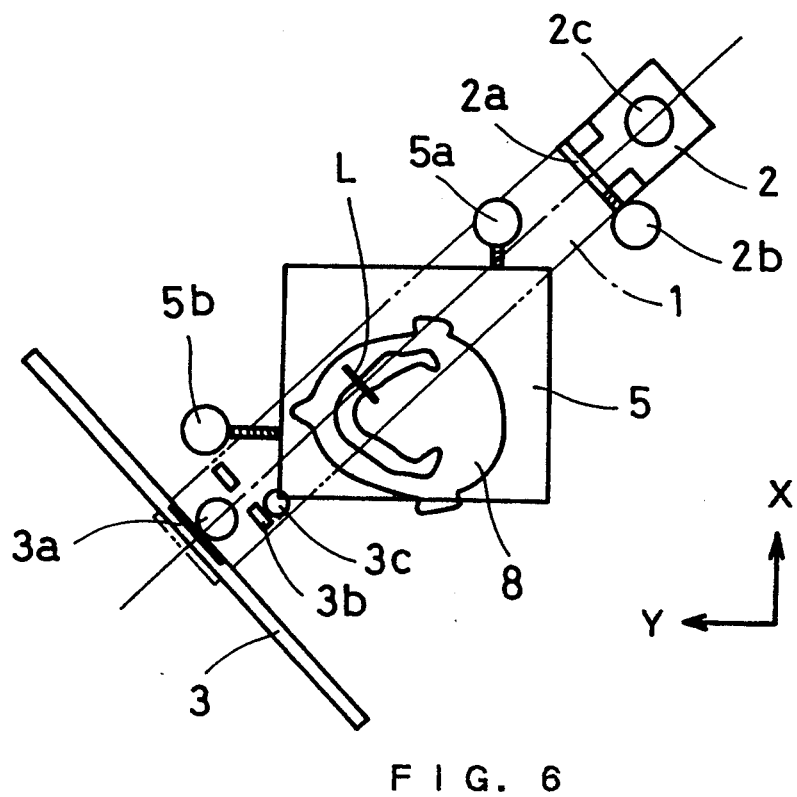
FIG. 6 is a view illustrating planigraphic photographing of still another plane by using the embodiment.

In addition, without rotating the X-Y table 5, it is possible to move the rotary arm 1 parallel to the planigraphic plane L by combining the X-axis movement and the Y-axis movement of the X-Y table 5 after the rotary arm 1 is set at a predetermined angle as shown in FIG. 6. Although this case causes the problem of making the control of the X-Y table 5 fairly complicated, the rotation base 6 is not necessary and the suspension mechanism for the rotary arm 1 can be made simple.

The above descriptions deal with only the movements in the horizontal planes. In actual practice, however, it is necessary to relatively move the X-ray beam and the head 8 of the patient in the vertical direction depending on the portion to be photographed. Although no adjustment means is shown for this movement, a means for vertically moving the entire apparatus or a means for vertically moving the patient and the patient supporting mechanism is installed as necessary.

Figure 7:
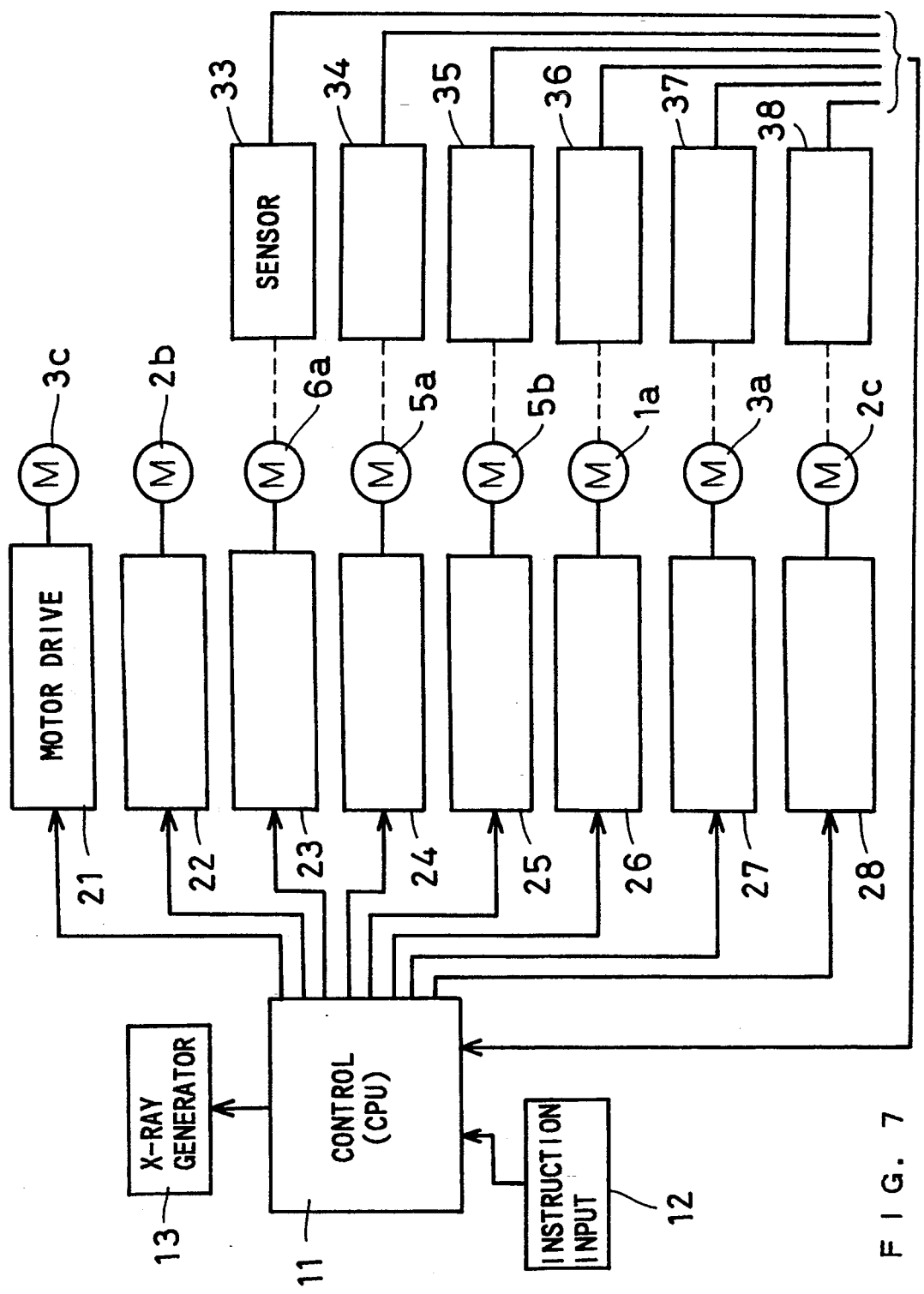
FIG. 7 is a block diagram illustrating the drive circuits of the embodiment.

FIG. 7 shows the drive circuits of the embodiment of the present invention. Numeral 11 represents a control section including a CPU, numeral 12 represents an operation instruction input circuit, numeral 13 represents an X-ray generator circuit, numerals 21 to 28 represent motor drive circuits, numerals 33 to 38 represent sensors for detecting positions and angles of various sections. When the operator inputs an instruction for indicating a photographing mode by operating the operation instruction input circuit 12, predetermined signals are output from the control section 11 to the motor drive circuits depending on the photographing mode (rotational tomographic photographing mode or planigraphic photographing mode). The motors are then driven and the movement results of the motors are detected by the sensors and fed back to the control section 11.

The film cassette 3 used for the embodiment is a flat-plate type including an ordinary X-ray film. Instead of using this type of X-ray detection surface, a flat-plate type radiographic sensitive element can also be used. Furthermore, instead of using a photosensitive element such as a film, an electrical detection device such as an X-ray CCD, an X-ray photoelectric conversion device or an X-ray fluorescent image intensifier can also be used. In case when such an electrical detection device is used as the X-ray detection surface, the same effect as that obtained by mechanically moving the X-ray detection surface can be obtained by using such an electrical image processing method as that disclosed by Japanese Patent Publication No. 2-29329, without moving the X-ray detection surface mechanically.

Figure 8A:
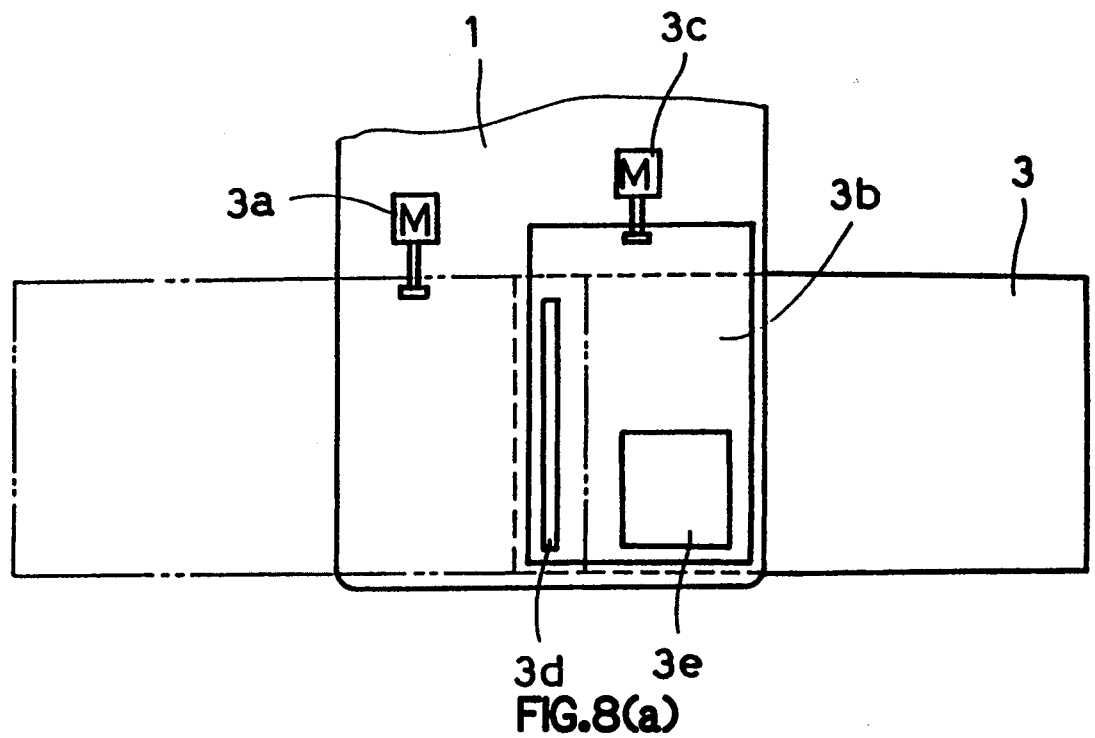
FIG. 8 is a view illustrating the operation condition of the film cassette of the embodiment.
Figure 8B:
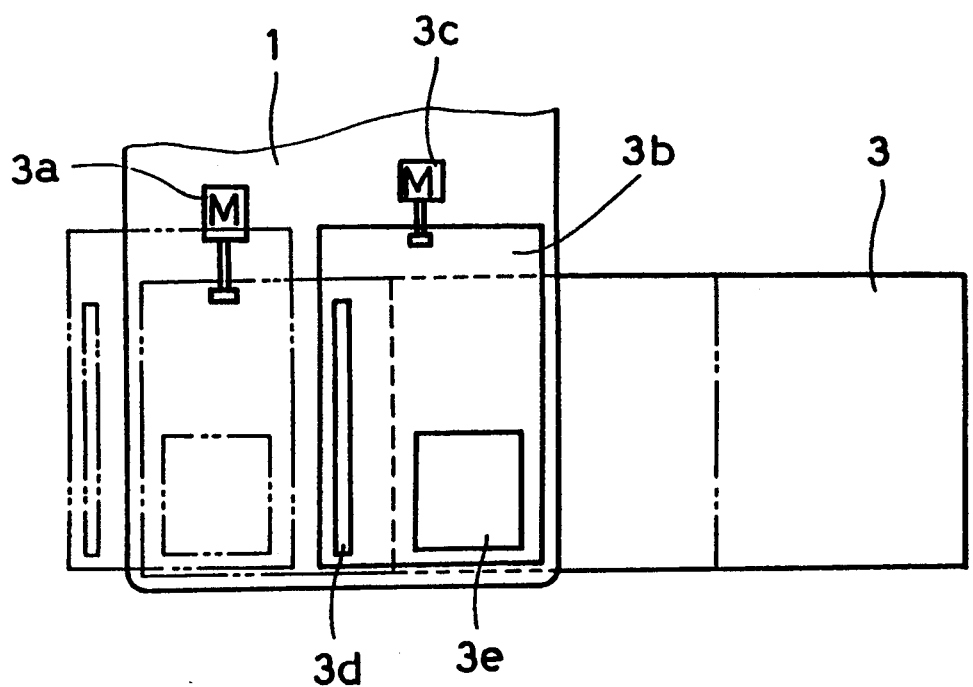

FIG. 8 shows the operation conditions of the film cassette 3 and the movement mechanisms thereof. More specifically, FIG. 8(a) shows the operation condition of rotational tomographic (panoramic) photographing, and FIG. 8(b) shows the operation condition of planigraphic photographing.

In the case of rotational tomographic photographing shown in FIG. 8(a), the beam-receiving shape changeover plate 3b is fixed to the rotary arm 1 and the film cassette 3 is moved by the movement drive motor 3a in synchronization with the rotation of the rotary arm 1. At this time, only the vertically-narrow, slit-shaped opening 3d for rotational tomographic photographing in the beam-receiving shape changeover plate 3b is opened by the motor 3c, and the opening 3e for planigraphic photographing is closed. On the other hand, in the case of planigraphic photographing shown in FIG. 8(b), the beam-receiving shape changeover plate 3b and the film cassette 3 are moved unitedly by the motors 3c and 3a respectively in synchronization with the rotation of the rotary arm 1. At this time, the opening 3d for rotational tomographic photographing in the beam-receiving shape changeover plate 3b is closed and only the opening 3e for planigraphic photographing is opened.

Although two separate motors, the beam-receiving shape changeover plate drive motor 3c and the film cassette drive motor 3a, are used in FIG. 8, a single motor can also be used for control. In addition, although a single motor, the motor 3c for driving the beam-receiving shape changeover plate 3b, is used in the embodiment, two separate motors can also be used to change the shape and to move the plate respectively. Furthermore, the changeover can be performed manually or by using a mechanism not shown in the figure.

Moreover, although the X-ray generator 2 of the embodiment shown in FIG. 1 is rotated relative to the rotary arm 1 by using the direction control motor 2c as a means for controlling the X-ray irradiation direction, only the irradiation field shape changeover plate 2a can be moved by a motor not shown in the figure in synchronization with the movement of the linear movement means, while the X-ray generator 2 is fixed to the rotary arm 1.

In the above-mentioned embodiment, the rotary arm 1 holds the X-ray source 2 and the film cassette 3 at the opposite ends thereof so that they face each other, the rotary arm 1 is moved linearly parallel to the planigraphic plane, the X-ray source 2 is rotated relative to the rotary arm 1, and the film cassette 3 is moved relative to the rotary arm 1 when performing planigraphic photographing in the above-mentioned embodiment. However, other structures are also possible. Table 1 below shows the combinations of these possible structures.

More specifically, in type A, the support member is not moved relative to the planigraphic plane but both the X-ray generator and the X-ray detection surface are moved. In type B, the support member is moved linearly parallel to the planigraphic plane, and at least one of the X-ray generator and the X-ray detection surface is moved. This type B can be converted into type C, wherein the X-ray generator is not moved relative to the support member but only the X-ray detection surface is moved, or into type D, wherein only the X-ray generator is moved relative to the support member, but the X-ray detection surface is not moved. The above-mentioned embodiment corresponds to type C. These types A to D correspond to claims 2 to 5 respectively.

TABLE 1

| Type | Movement of support member relative to planigraphic plane | Movement of X-ray generator relative to support member | Movement of X-ray detector relative to support member |
|---|---|---|---|
| A | Fixed | Linear movement and rotation | Linear movement |
| B | Parallel linear movement | Linear movement and rotation of at least one unit | Linear movement of at least one unit |
| C | Parallel linear movement | Rotation at fixed position | Linear movement |
| D | Parallel linear movement | Linear movement and rotation | Fixed |

Next, these four types of embodiments will be explained referring to FIGS. 9 to 12. Although the rotary arm 1 is used as the support member in each figure, it is not necessary to rotate the rotary arm 1 in the case of planigraphic photographing.

Figure 9:
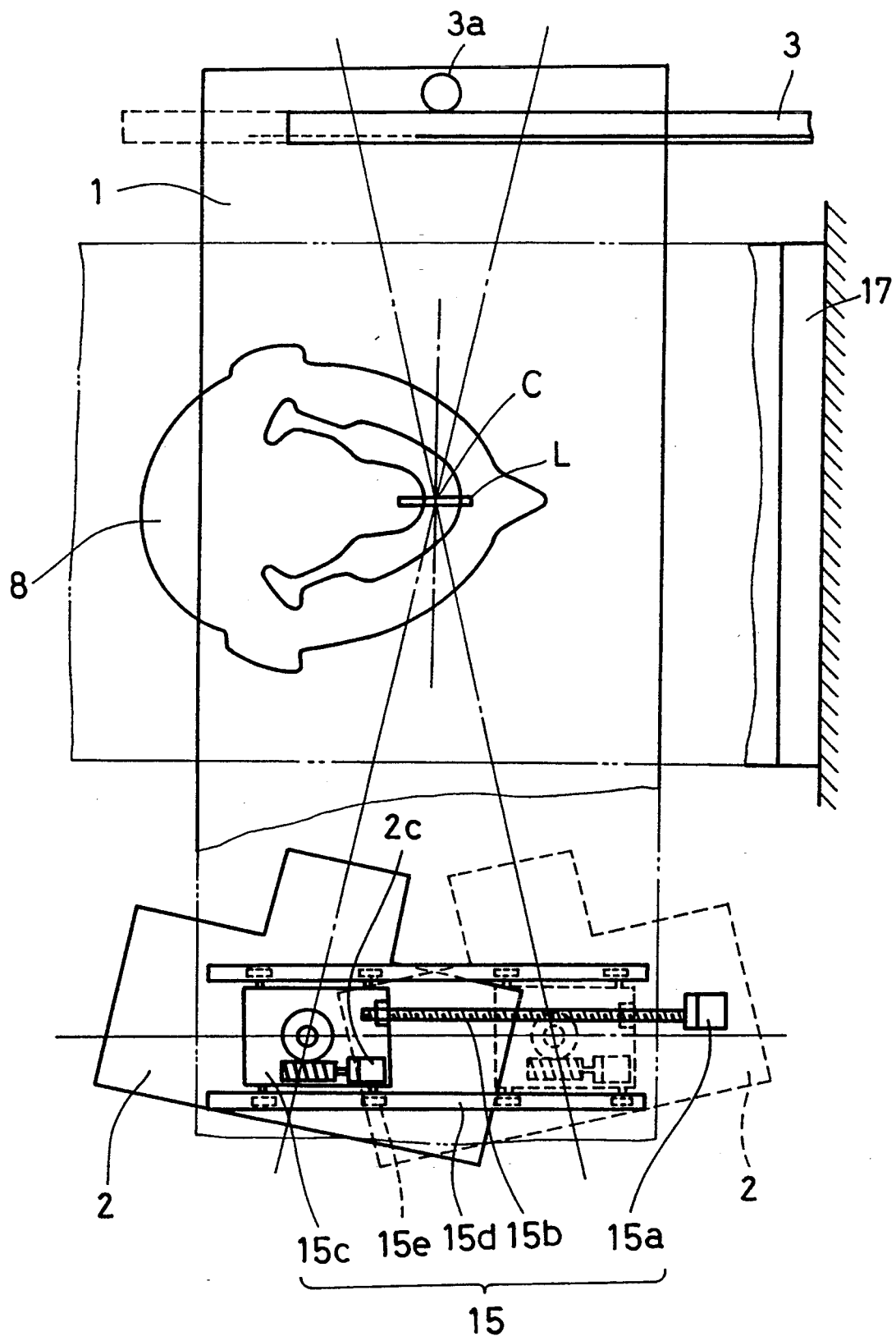
FIGS. 9 to 12 are schematic plan views illustrating the entire structures of other embodiments in accordance with the present invention.

The embodiment shown in FIG. 9 corresponds to type A. Referring to FIG. 9, numeral 15a represents a movement drive motor provided in the rotary arm 1. An output shaft 15b is threaded into a movement plate 15c which supports the X-ray source 2. Numeral 15d represents rails provided on the rotary arm 1, numeral 15e represents rollers provided on the movement plate 15c, and numeral 15 represents the linear movement means for the X-ray source 2, which are composed of the above-mentioned components. When the movement drive motor 15a is activated, the output shaft 15b is rotated and the movement plate 15c is moved along the rails 15d. In synchronization with this movement, the movement drive motor 3a which functions as the linear movement mechanism for the film cassette 3 is activated to move the film cassette 3. Furthermore, in synchronization with this movement, the motor 2c is activated to rotate the X-ray source 2 so that the central axis of the X-ray beam is controlled to always passes the center C of the planigraphic plane L.

Figure 10:
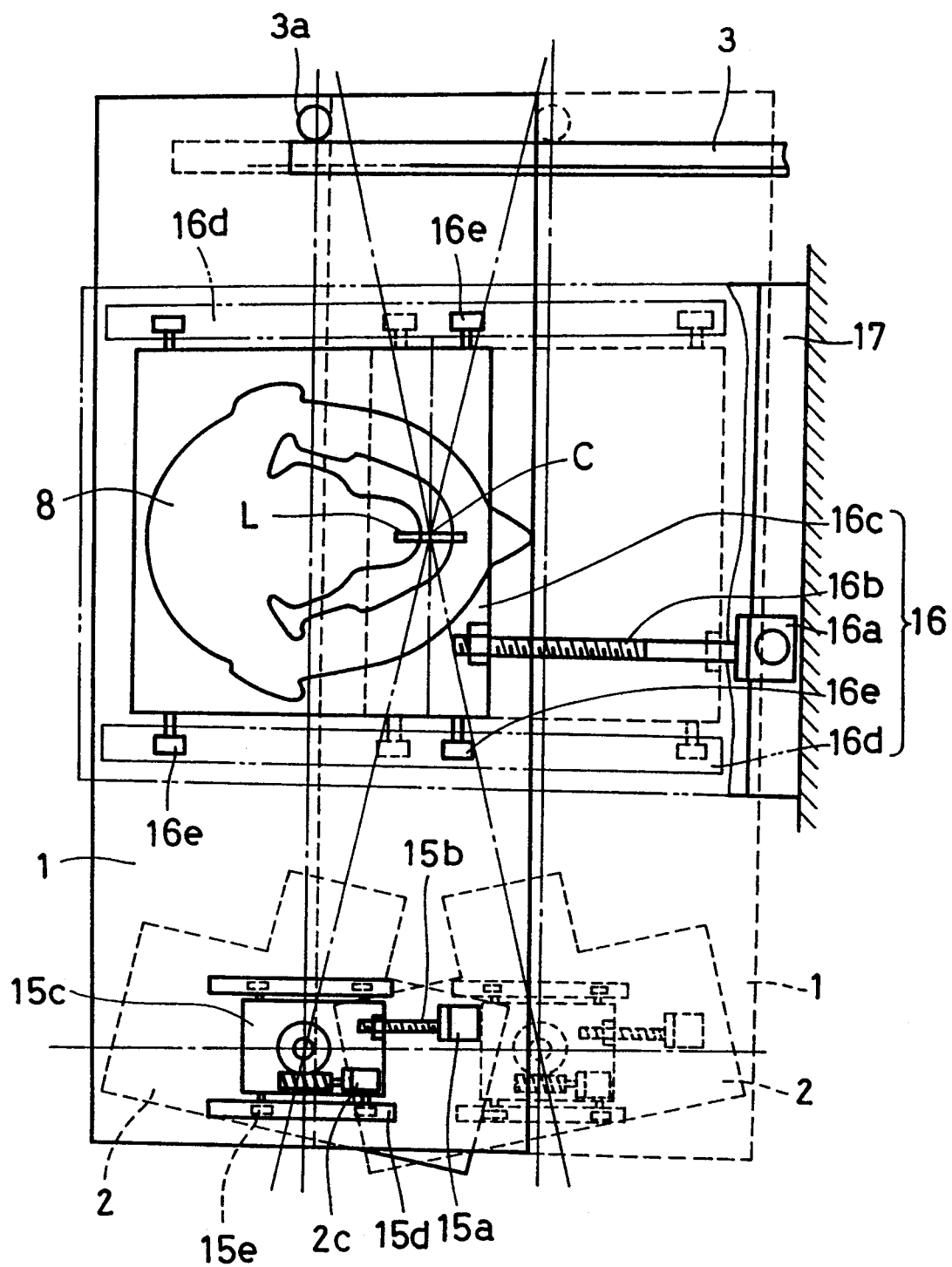

The embodiment shown in FIG. 10 corresponds to type B. Since the rotary arm 1 is moved in this embodiment, the mechanism similar to that used for the movement mechanism of the X-ray source 2 shown in FIG. 9 is provided. More specifically, numeral 16 represents the linear movement mechanism of the rotary arm 1, numeral 16a represents a movement drive motor provided on a fixture member 17, numeral 16b represents the output shaft of the motor, numeral 16c represents a movement member for supporting the rotary arm 1, numeral 16d represents rails provided on the fixture member 17, and numeral 16e represents rollers provided on the movement member 16c. When the movement drive motor 16a is activated, the movement member 16c is moved along the rails 16d.

FIG. 10 also shows an embodiment wherein both the X-ray source 2 and the film cassette 3 are moved. The mechanism for moving and rotating the X-ray source 2 is similar to that shown in FIG. 9. Since the rotary arm 1 which functions as a support member is moved in this embodiment, the movement distance of the X-ray source 2 relative to the rotary arm 1 is made smaller, and the movement distance of the film cassette 3, which is opposite to the movement direction of the rotary arm 1, is made larger.

Figure 11:
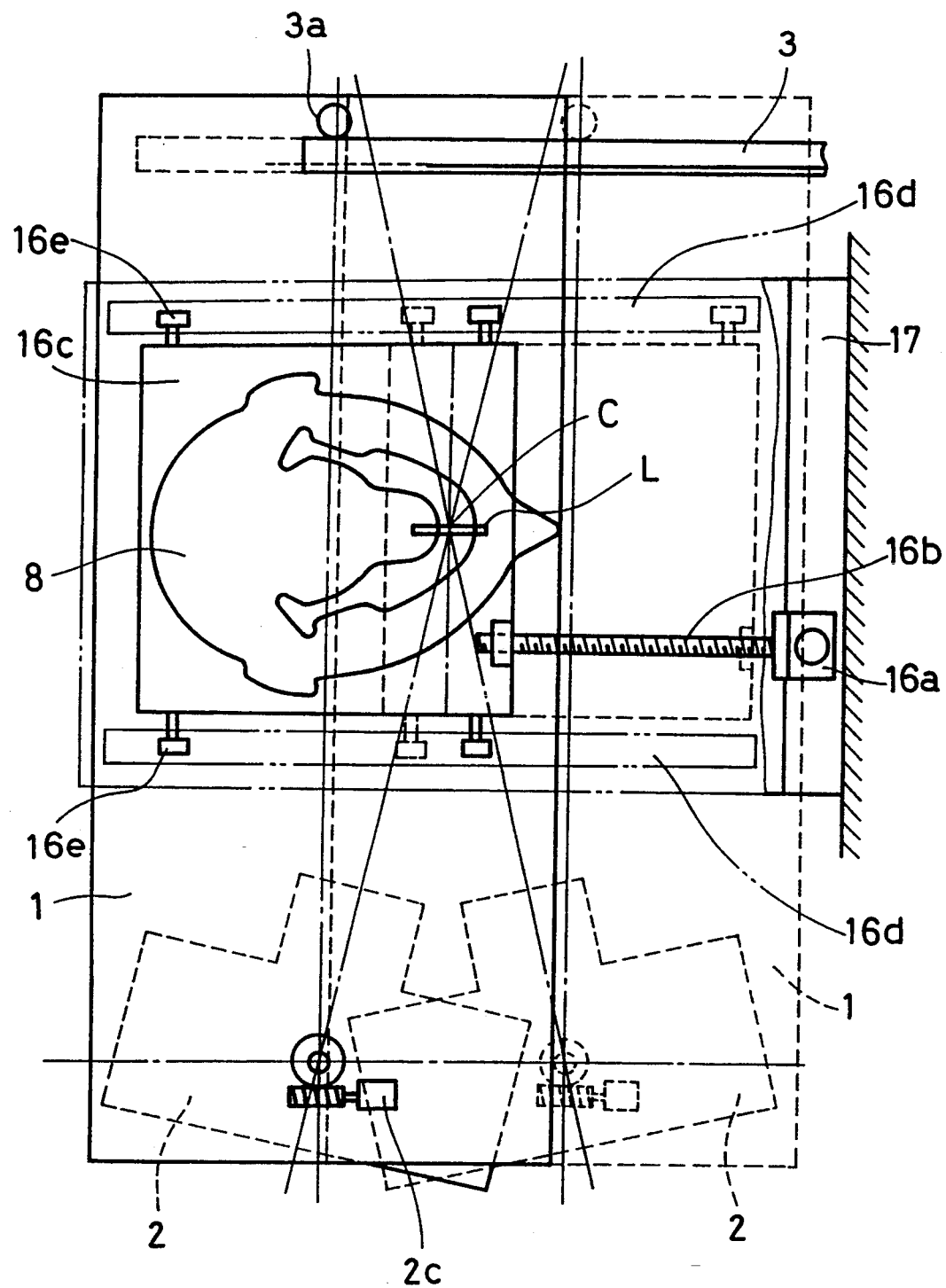

The embodiment shown in FIG. 11 corresponds to type C. Since only a rotation mechanism is provided for the X-ray source 2, the movement distance of the film cassette 3 is made larger than that in the case of the embodiment shown in FIG. 10.

Figure 12:
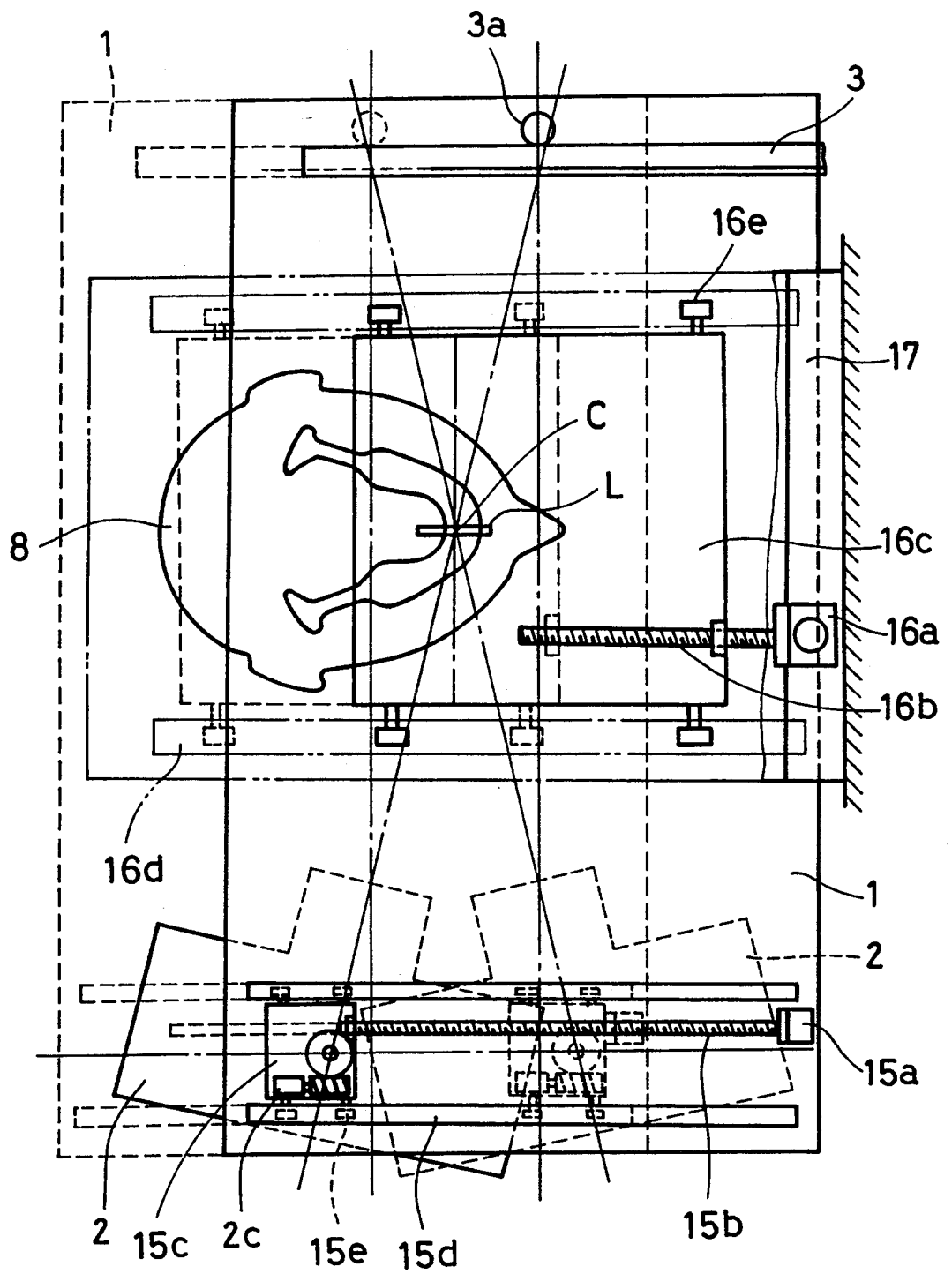

The embodiment shown in FIG. 12 corresponds to type D. Although the film cassette 3 is fixed to the rotary arm 1 and a mechanism which moves and rotates the X-ray source 2 relative to rotary arm 1 is provided, the movement distance of the X-ray sources 2 is made larger than that in the case of the embodiment shown in FIG. 10.

FIGS. 9 to 12 are provided to illustrate the basic structures of the types listed in Table 1. Although the movement drive motor 16a, the movement member 16c and the fixture member 17 correspond to the movement drive motor 5a or 5b, the X-Y table 5 and the pedestal base 7 respectively shown in FIGS. 1 and 2, these members are shown simply to prevent the figures from becoming complicated. In addition, although the X-Y table 5 and the movement mechanisms 15 and 16, which function as linear movement means for the rotary arm 1 and the X-ray source 2 are composed of motors, threaded shafts, rollers and rails, etc., other known linear movement mechanisms, such as a motor-driven wire mechanism and a motor-pinion-rack combination mechanism, can also be adopted as necessary, instead of the threaded shaft mechanism.

Figure 13A:
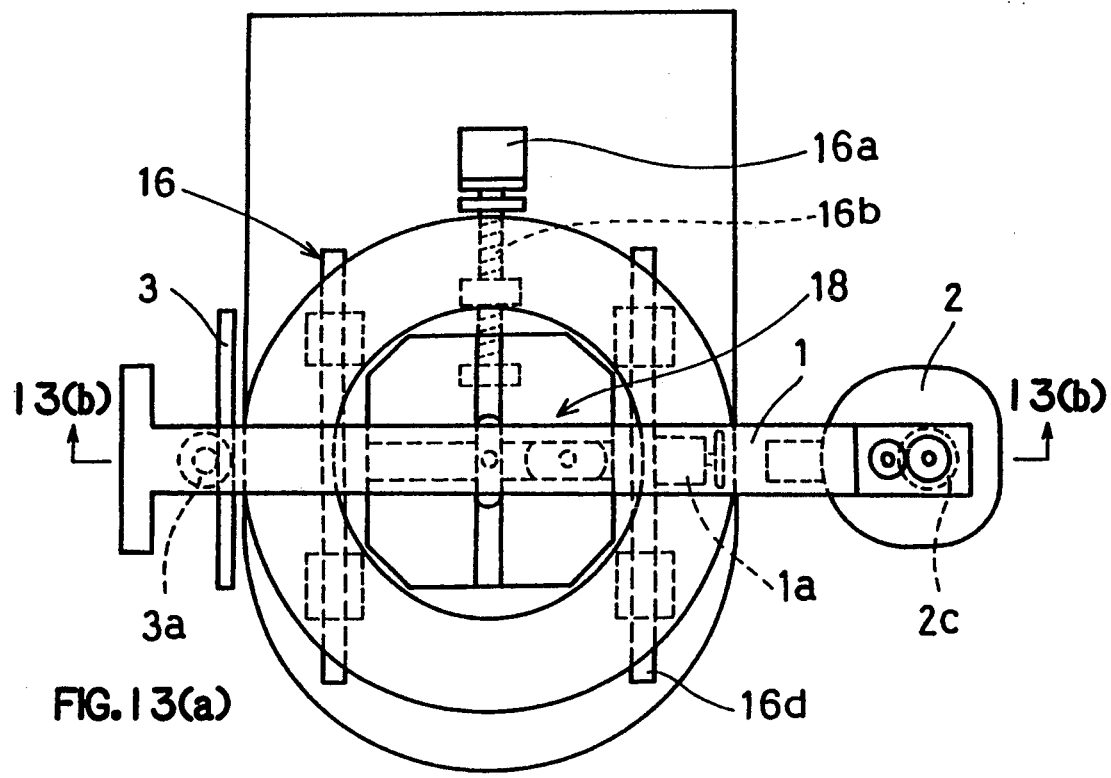
Figure 13B:
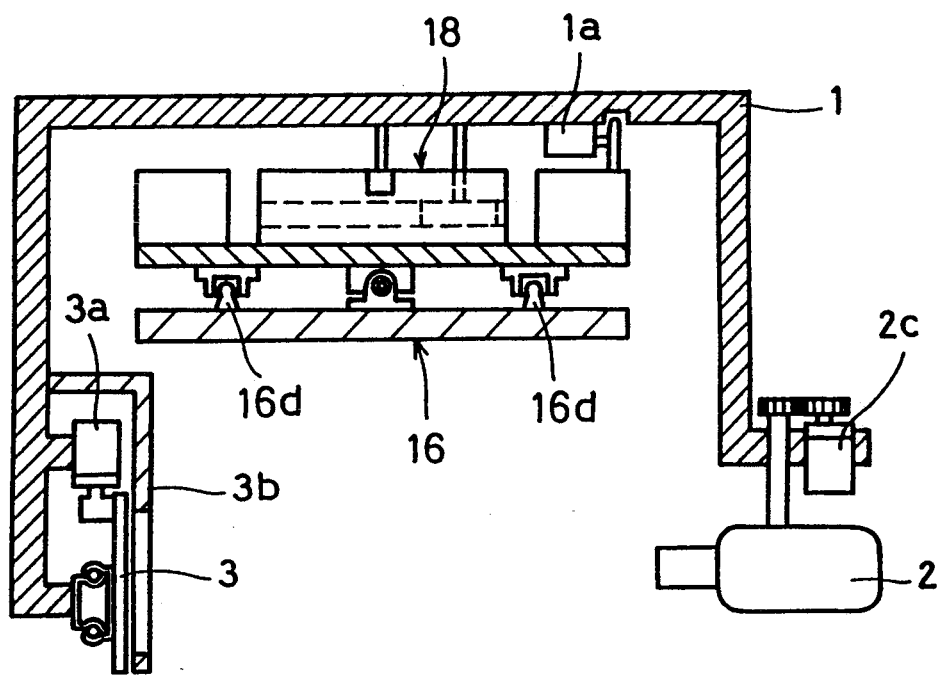
Figure 14A:
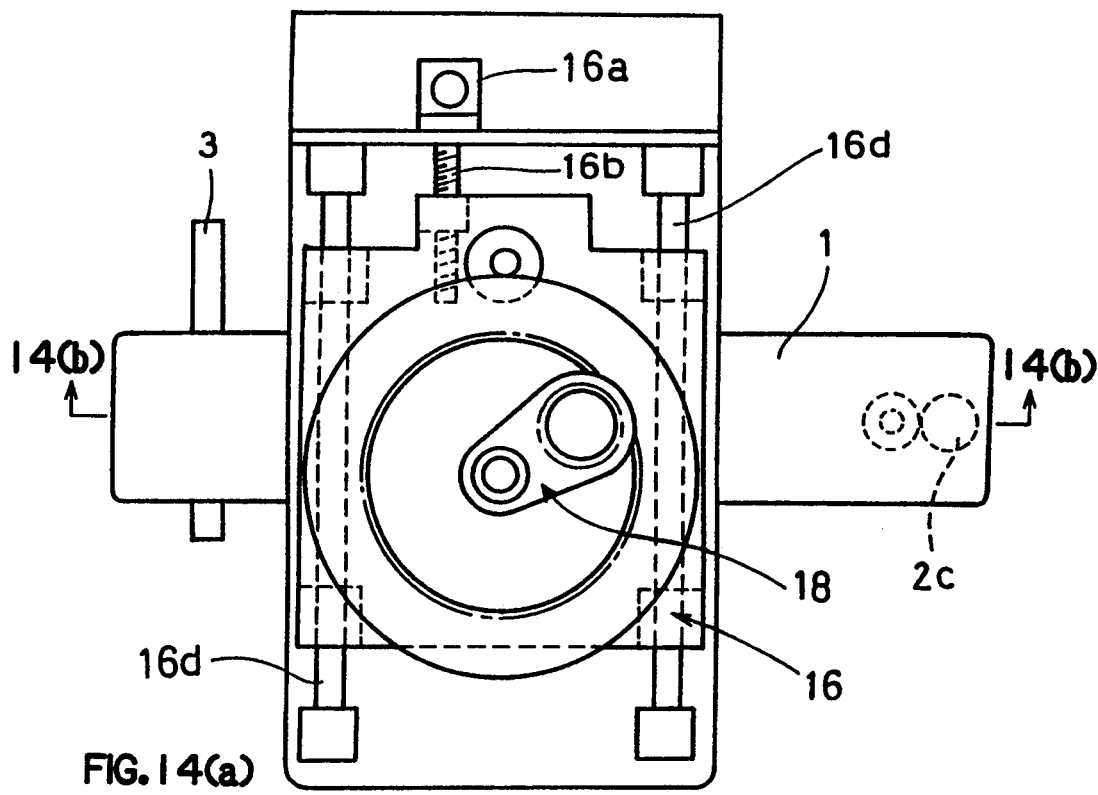
Figure 14B:
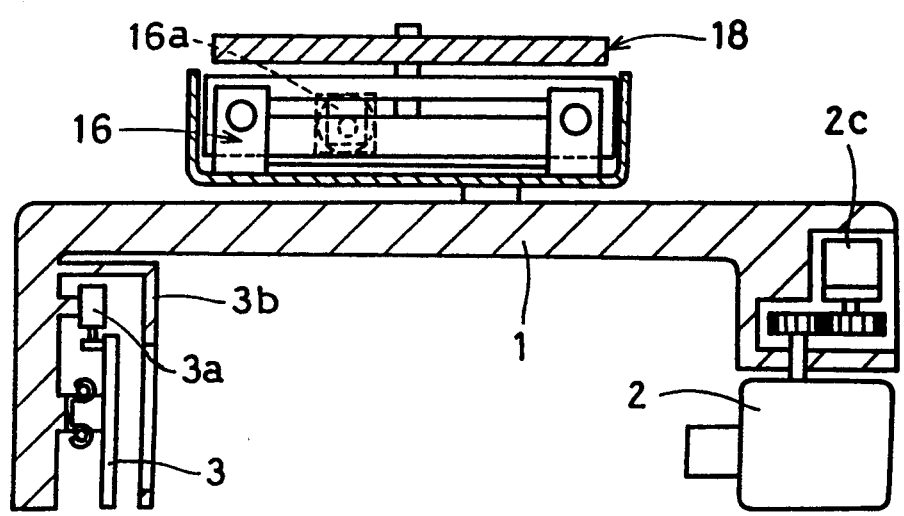
Figure 15A:
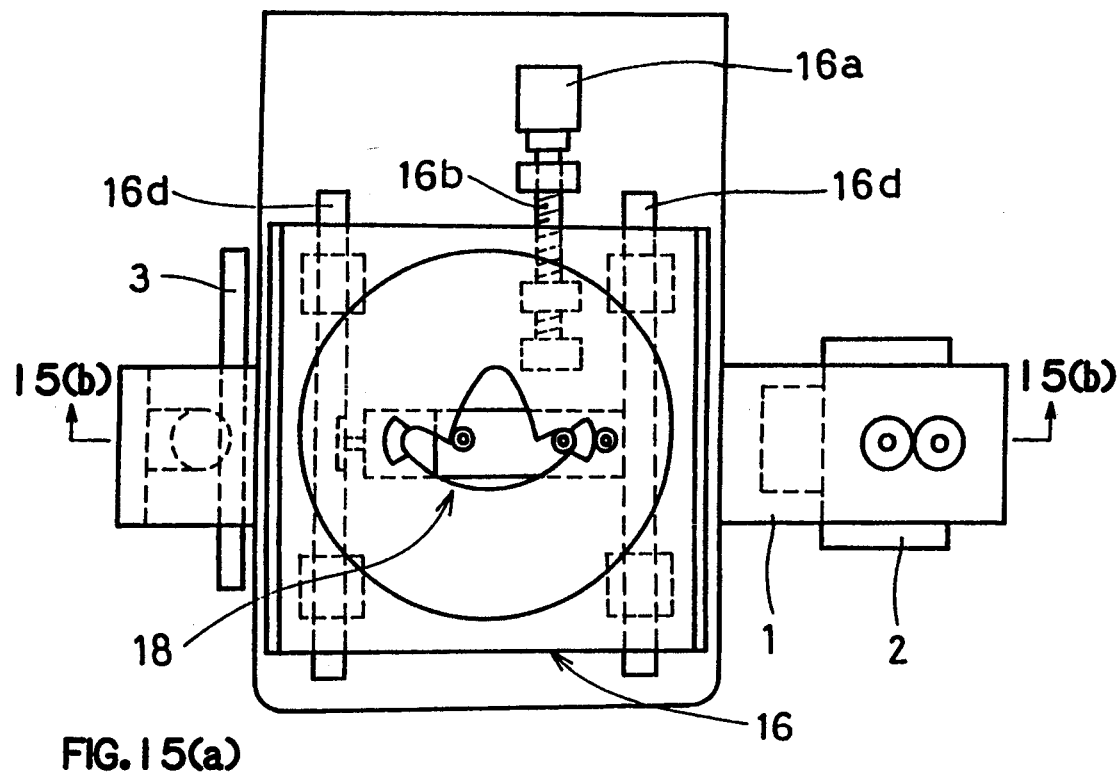
Figure 15B:
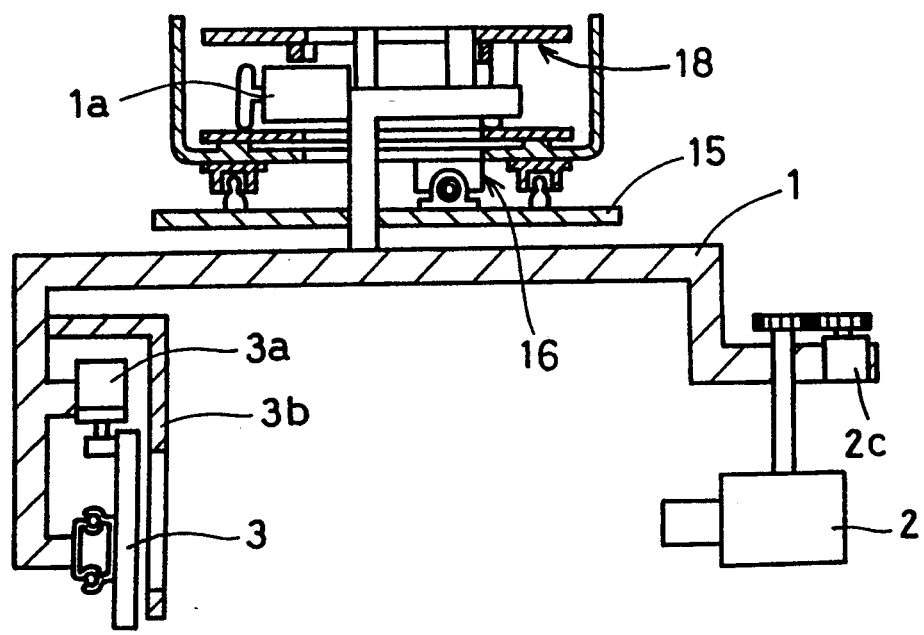
Figure 16A:
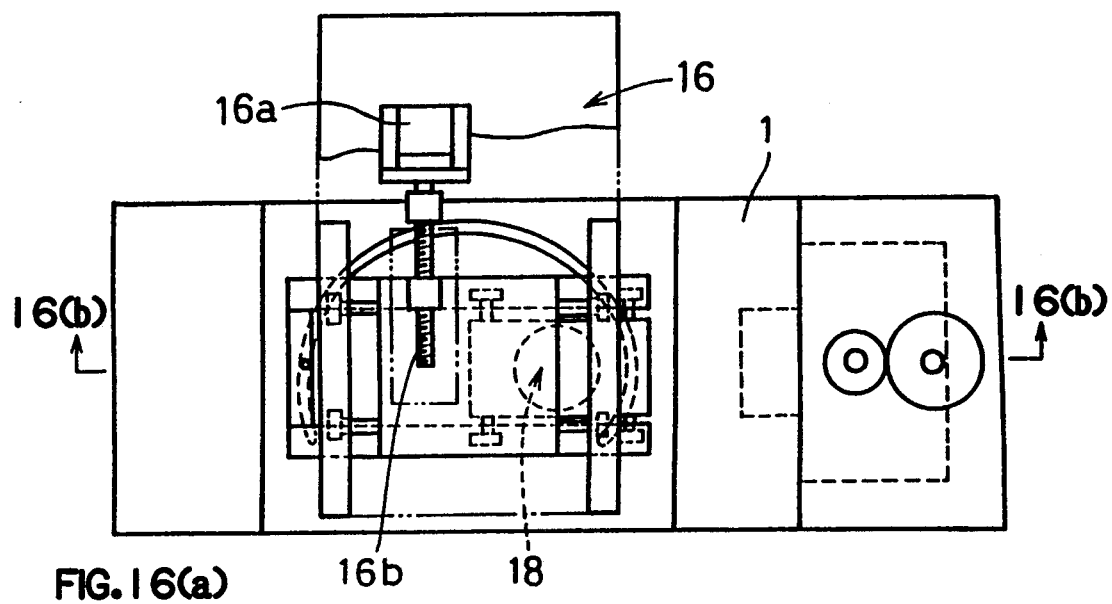
Figure 16B:
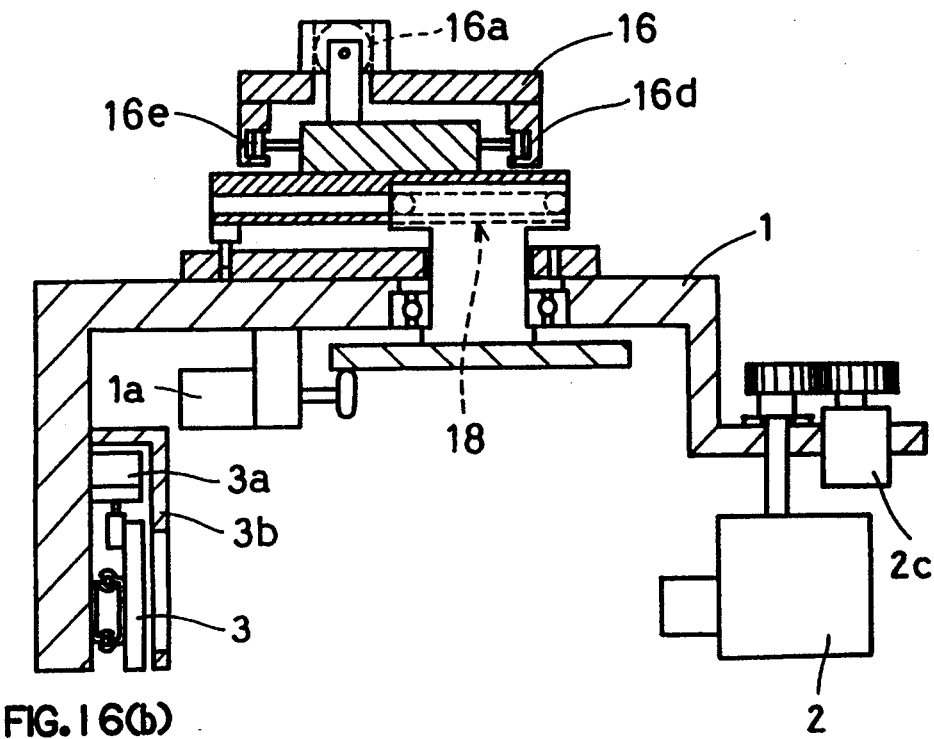

FIGS. 13 to 19 show embodiments classified as type C listed in Table 1. In these embodiments, mechanisms other than the X-Y table are adopted as the mechanism 18 for positioning control of rotation center for controlling the rotation center position of the rotary arm 1 during rotational tomographic photographing. FIG. 13 shows a mechanism for ellipsopantomography with crossing grooves, FIG. 14 shows a planetary gear mechanism, and FIG. 15 shows a mechanism for three differential pivots circles tomography; these are used respectively as the mechanism 18 for positioning control of rotation center. FIGS. 16 to 19 also show different mechanisms, which are used respectively as the mechanism 18 for positioning control of rotation center. Since these mechanisms used as the mechanism 18 for positioning control of rotation center for rotational tomographic photographing are known, they are not detailed here. All of these mechanisms are additionally provided with the devices for performing planigraphic photographing by the present invention.

Figure 17B:
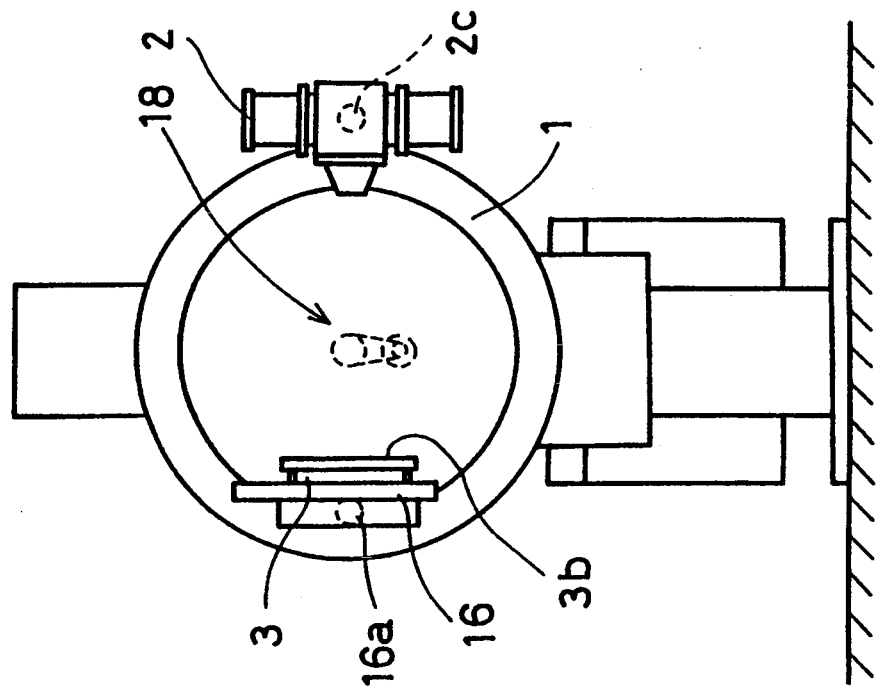
FIG. 17(a) is a side view illustrating the mechanism and FIG. 17(b) is a front view illustrating the mechanism.
Figure 17A:
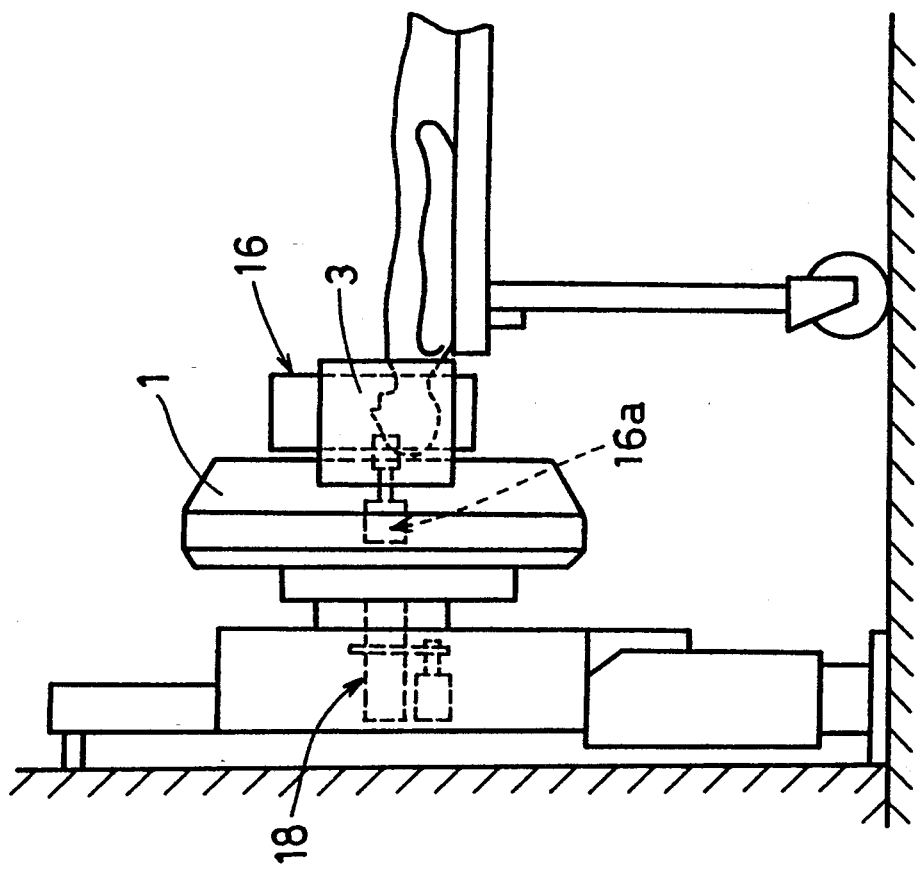
Figure 18A:
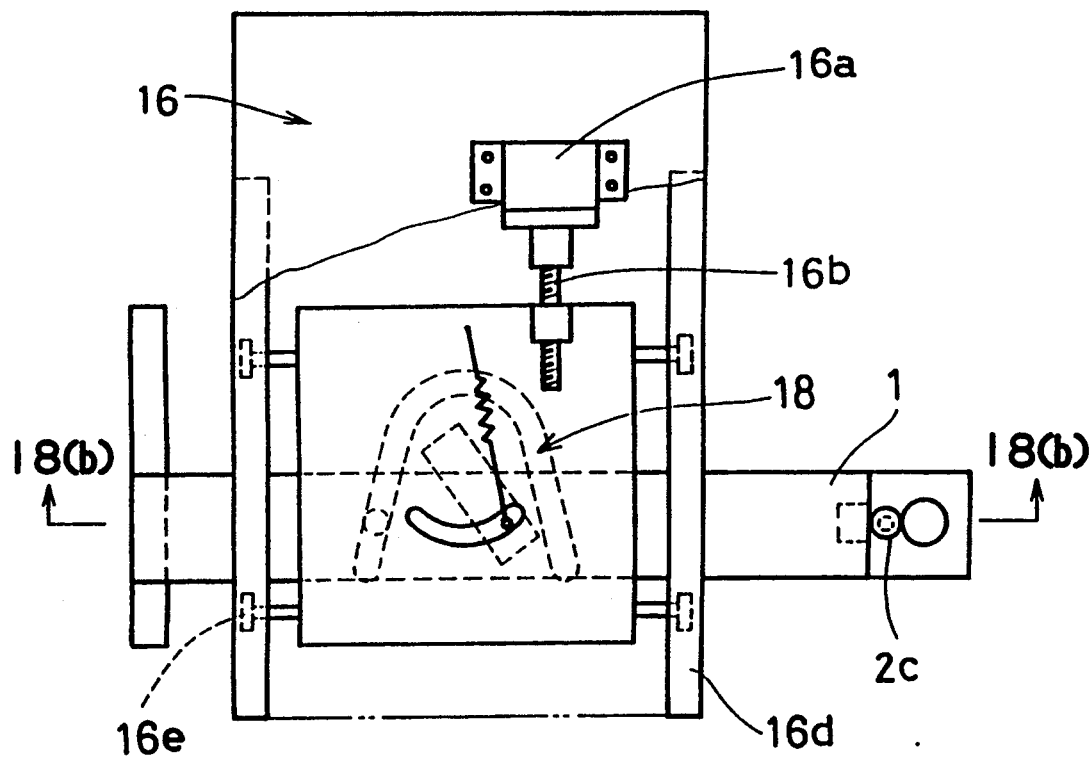
FIG. 18(a) is a side view illustrating the mechanism and FIG. 18(b) is a cross-sectional view taken on line A—A of FIG. 18(a).
Figure 18B:
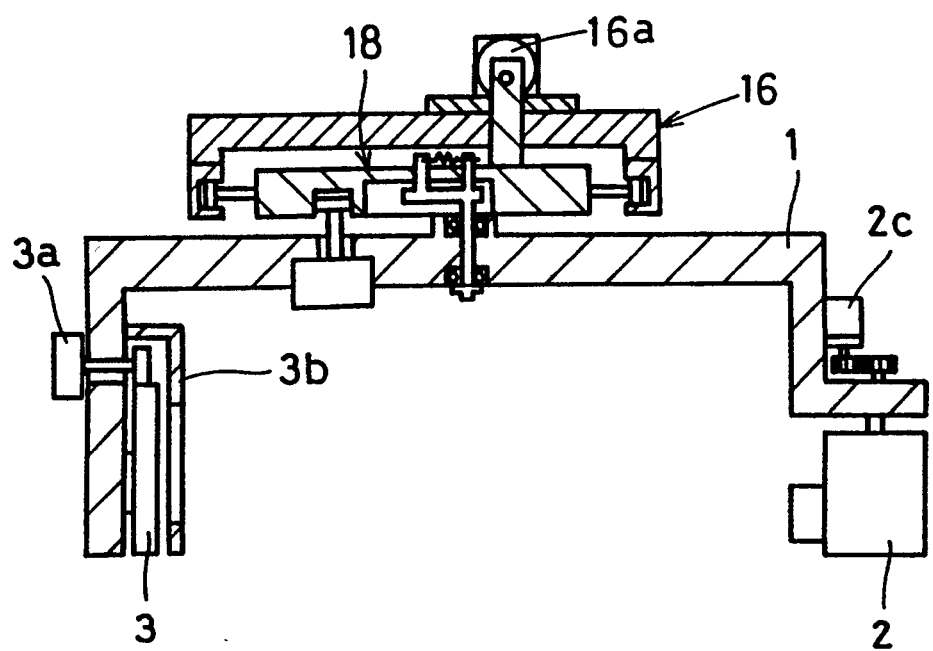
Figure 19:
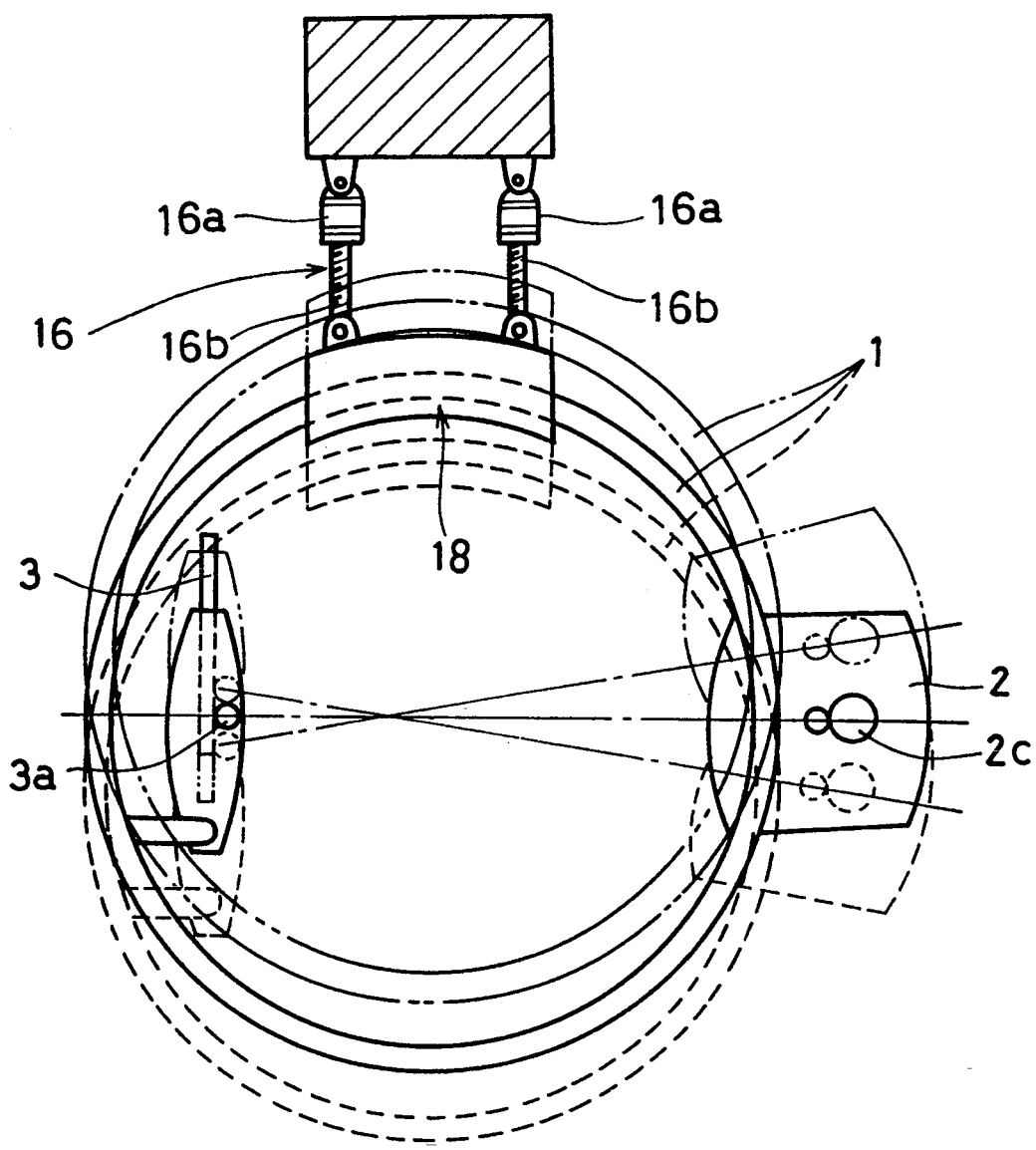
FIG. 19 is a schematic plan view illustrating the structure of the mechanism for positioning control of rotation center of yet another embodiment.

More particularly, in the embodiments shown in the figures other than FIG. 17, the linear movement means 16 of the threaded-shaft type comprising the movement drive motor 16a, the threaded shaft 16b, etc. is added to permit planigraphic photographing, so that the rotary arm 1 can be moved parallel to the planigraphic plane. The embodiment shown in FIG. 17 is additionally provided with the linear movement means 16 of a friction wheel type to linearly move the X-ray detection surface 3 up and down by using the movement drive motor 16a.

In these embodiments, the rotation base 6 and the motor 6a for rotating the rotation base 6 can also be provided to rotate the mechanism 18 for positioning control of rotation center and the support member attached thereto relative to the pedestal base 7 in the manner similar to that shown in FIG. 1, although these are not shown in FIGS. 13 to 19. Furthermore, the irradiation field shape changeover plate 2a and the changeover drive motor 2b can also be provided as necessary.

Accordingly, planigraphic photographing can be performed without rotating the support member, thereby causing little or no distortion in X-ray images. Besides, since planigraphic photographing can be performed at any position by changing the velocity ratio of the relative movements between the X-ray generator and the X-ray detection surface, the magnifying ratios of X-ray images for planigraphic photographing can be changed as desired by setting the head of the patient at the position. Furthermore, the X-ray detection surface can be maintained easily parallel to the planigraphic plane and the photographing apparatus can also be positioned easily relative to the patient. Moreover, when the apparatus is equipped with a rotary arm, the apparatus has the advantage of requiring fewer members to be added for planigraphic photographing by utilizing the rotary arm as a support member, thereby capable of offering a rotational tomographic X-ray apparatus with planigraph function at a relatively low cost.

In the case of an embodiment wherein the support member and the mechanism for positioning control of rotation center are made rotatable relative to the pedestal base by using the rotation base, the photographing apparatus can be positioned quickly to a place suited for photographing the planigraphic plane having a given direction by rotating the support member, without moving the patient, thereby further enhancing convenience.

In addition, particularly during planigraphic photographing, by providing the irradiation field shape changeover means and the beam-receiving shape changeover means, a plurality of different planigraphic planes can be photographed on a single film, thereby capable of reducing X-ray exposure and efficiently utilizing X-ray films.

What is claimed is:

1. In a rotational tomographic X-ray apparatus structured to obtain rotational tomographic images of maxillofacial regions by rotating an X-ray generator and an X-ray detection surface disposed opposite to each other with the head of a patient positioned therebetween while maintaining a constant relationship therebetween and by moving said X-ray detection surface substantially perpendicular to the direction of the X-rays irradiated from said X-ray generator in synchronization with the rotation, a rotational tomographic X-ray apparatus with planigraph function having said X-ray detection surface disposed parallel to a planigraphic plane selected as a subject to be photographed, and comprising a linear movement means for moving said X-ray generator and said X-ray detection surface synchronously in relatively opposite directions parallel to said planigraphic plane and an X-ray irradiation direction control means for controlling the X-ray irradiation direction so that the irradiated X-rays always pass the same specific region in said planigraphic plane and are incident on said X-ray detection surface in synchronization with the linear movement.

2. A rotational tomographic X-ray apparatus with planigraph function as claimed in claim 1, further comprising a support member for supporting said X-ray generator and said X-ray detection surface disposed opposite to each other with said planigraphic plane positioned therebetween, and being structured to move both said X-ray generator and said X-ray detection surface linearly relative to said support member by using said linear movement means and to rotate said X-ray generator toward said X-ray detection surface by using said X-ray irradiation direction control means.

3. A rotational tomographic X-ray apparatus with planigraph function as claimed in claim 1, further comprising a support member for supporting said X-ray generator and said X-ray detection surface disposed opposite to each other with said planigraphic plane positioned therebetween, and being structured to move said support member linearly parallel to said planigraphic plane and to move at least one of said X-ray generator and said X-ray detection surface relative to said support member by using said linear movement means, and also to rotate said X-ray generator toward said X-ray detection surface by using said X-ray irradiation direction control means.

4. A rotational tomographic X-ray apparatus with planigraph function as claimed in claim 3, wherein said X-ray generator is moved together with said support member and only said X-ray detection surface is moved linearly relative to said support member.

5. A rotational tomographic X-ray apparatus with planigraph function as claimed in claim 3, wherein said X-ray detection surface is moved together with said support member and only said X-ray generator is moved linearly relative to said support member.

6. A rotational tomographic X-ray apparatus with planigraph function as claimed in claim 2, 3, 4 or 5, wherein said support member is a rotary arm.

7. A rotational tomographic X-ray apparatus with planigraph function as claimed in claim 6, wherein said rotary arm is moved parallel to said planigraphic plane by a mechanism for positioning control of rotation center for controlling the rotation center of said rotary arm.

8. A rotational tomographic X-ray apparatus with planigraph function as claimed in claim 7, further comprising a rotation means for rotating said mechanism for positioning control of rotation center as desired.

9. A rotational tomographic X-ray apparatus with planigraph function as claimed in claim 1, 2, 3, 4 or 5, further comprising, on the side of said X-ray generator, an irradiation field shape changeover means for changing the irradiation shape of the X-ray beam irradiated from said X-ray generator depending on the mode of photographing, and also comprising, on the side of said X-ray detection surface, a beam-receiving shape changeover means for changing the beam-receiving shape of the X-ray beam being incident on said X-ray detection surface depending on the mode of photographing.

10. A rotational tomographic X-ray apparatus with planigraph function as claimed in claim 9, further comprising a movement means for automatically moving said beam-receiving changeover means in synchronization with the movement of said X-ray detection surface.

11. A rotational tomographic X-ray apparatus with planigraph function as claimed in claim 1, 2, 3, 4 or 5, wherein said X-ray detection surface is an X-ray film cassette or an X-ray radiographic photosensitive element.

12. A rotational tomographic X-ray apparatus with planigraph function as claimed in claim 1, 2, 3, 4 or 5, wherein said X-ray detection surface is an X-ray CCD, an X-ray photoelectric conversion device or an X-ray fluorescent image intensifier, and the detection region of said X-ray detection surface is moved by electrically processing images obtained by these devices.

13. A rotational tomographic X-ray apparatus with planigraph function as claimed in claim 6, further comprising, on the side of said X-ray generator, an irradiation field shape changeover means for changing the irradiation shape of the X-ray beam irradiated from said X-ray generator depending on the mode of photographing, and also comprising, on the side of said X-ray detection surface, a beam-receiving shape changeover means for changing the beam-receiving shape of the X-ray beam being incident on said X-ray detection surface depending on the mode of photographing.

14. A rotational tomographic X-ray apparatus with planigraph function as claimed in claim 7, further comprising, on the side of said X-ray generator, an irradiation field shape changeover means for changing the irradiation shape of the X-ray beam irradiated from said X-ray generator depending on the mode of photographing, and also comprising, on the side of said X-ray detection surface, a beam-receiving shape changeover means for changing the beam-receiving shape of the X-ray beam being incident on said X-ray detection surface depending on the mode of photographing.

15. A rotational tomographic X-ray apparatus with planigraph function as claimed in claim 8, further comprising, on the side of said X-ray generator, an irradiation field shape changeover means for changing the irradiation shape of the X-ray beam irradiated from said X-ray generator depending on the mode of photographing, and also comprising, on the side of said X-ray detection surface, a beam-receiving shape changeover means for changing the beam-receiving shape of the X-ray beam being incident on said X-ray detection surface depending on the mode of photographing.

16. A rotational tomographic X-ray apparatus with planigraph function as claimed in claim 13, further comprising a movement means for automatically moving said beam-receiving changeover means in synchronization with the movement of said X-ray detection surface.

17. A rotational tomographic X-ray apparatus with planigraph function as claimed in claim 14, further comprising a movement means for automatically moving said beam-receiving changeover means in synchronization with the movement of said X-ray detection surface.

18. A rotational tomographic X-ray apparatus with planigraph function as claimed in claim 15, further comprising a movement means for automatically moving said beam-receiving changeover means in synchronization with the movement of said X-ray detection surface.

* * * * *